United States Patent [19]

Elbe et al.

[11] Patent Number: 5,045,108
[45] Date of Patent: Sep. 3, 1991

[54] HERBICIDAL AND PLANT GROWTH-REGULATING N-ARYL-PYRROL-L-ONE AND ISOINDOL-2-ONE COMPOUNDS

[75] Inventors: Hans-Ludwig Elbe, Wuppertal; Albrecht Marhold, Leverkusen; Klaus Lürssen, Bergisch Gladbach; Hans-Joachim Santel, Leverkusen; Robert R. Schmidt; Birgit Krauskopf, both of Bergisch Gladbach, all of Fed. Rep. of Germany

[73] Assignee: Bayer Aktiengesellschaft, Leverkusen, Fed. Rep. of Germany

[21] Appl. No.: 534,383

[22] Filed: Jun. 7, 1990

[30] Foreign Application Priority Data

Jun. 21, 1989 [DE] Fed. Rep. of Germany ....... 3920271

[51] Int. Cl.$^5$ .................. A01N 43/36; A01N 43/38; C07D 207/38; C07D 209/46
[52] U.S. Cl. .................................. 71/94; 548/452; 548/543
[58] Field of Search .................. 548/452, 543; 71/92

[56] References Cited

U.S. PATENT DOCUMENTS 3,992,189 11/1976 Goddard .

FOREIGN PATENT DOCUMENTS 305333 3/1989 European Pat. Off. .

Primary Examiner—David B. Springer
Attorney, Agent, or Firm—Sprung Horn Kramer & Woods

[57] ABSTRACT

Herbicidal and plant growth-regulating N-aryl-nitrogen heterocyclic compounds of the formula

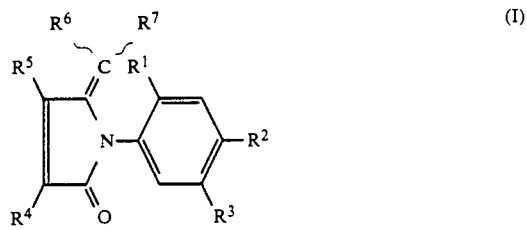

in which
$R^1$ represents hydrogen or halogen,
$R^2$ represents cyano, nitro, fluorine, chlorine, bromine, iodine, alkyl, halogenoalkyl, alkoxy, halogenoalkoxy, alkylthio or halogeneoalkylthio,
$R^3$ represents halogen, hydroxyl or mercapto, or represents a radical, in each case optionally substituted, from the series comprising alkoxy, alkenyloxy, alkinyloxy, cycloalkoxy, alkylthio, alkenylthio, alkinylthio and cycloalkylthio,
$R^4$ represents hydrogen, halogen or alkyl,
$R^5$ represents hydrogen, halogen or alkyl, or together with $R^4$ represents alkanediyl,
$R^6$ represents hydrogen or alkyl and
$R^7$ represents hydrogen or alkyl, or together with $R^6$ represents alkanediyl, with certain provisos regarding $R^2$.

17 Claims, No Drawings

HERBICIDAL AND PLANT GROWTH-REGULATING N-ARYL-PYRROL-L-ONE AND ISOINDOL-2-ONE COMPOUNDS

The present invention relates to new N-aryl-nitrogen heterocyclic compounds, several processes and new intermediate products for their preparation and their use as herbicides and plant growth regulators.

It is known that certain N-aryl-nitrogen heterocyclic compounds have herbicidal properties (compare, for example, U.S. Pat. No. 3,992,189; EP-A 305,333; JP-A 63-39859 and citation in Chem. Abstracts 109, 37735p). However, the herbicidal action of the already known compounds, like their tolerance in respect of important crop plants, is not completely satisfactory in all fields of use.

The new N-aryl-nitrogen heterocyclic compounds of the general formula (I)

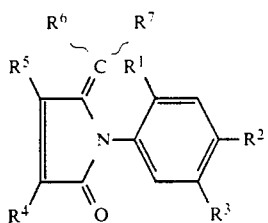

in which
$R^1$ represents hydrogen or halogen,
$R^2$ represents cyano, nitro, fluorine, chlorine, bromine, iodine, alkyl, halogenoalkyl, alkoxy, halogenoalkoxy, alkylthio or halogenoalkylthio,
$R^3$ represents halogen, hydroxyl or mercapto, or represents a radical, in each case optionally substituted, from the series comprising alkoxy, alkenyloxy, alkinyloxy, cycloalkoxy, alkylthio, alkenylthio, alkinylthio and cycloalkylthio,
$R^4$ represents hydrogen, halogen or alkyl,
$R^5$ represents hydrogen, halogen or alkyl, or together with $R^4$ represents alkanediyl,
$R^6$ represents hydrogen or alkyl and
$R^7$ represents hydrogen or alkyl, or together with $R^4$ represents alkanediyl,
with the proviso that $R^2$ only represents chlorine if either
(a) $R^1$ represents hydrogen or at least one of the radicals $R^4$, $R^5$, $R^6$ and $R^7$ represents alkyl and at the same time
$R^3$ represents halogen or mercapto or represents a radical, in each case optionally substituted, from the series comprising alkylthio, alkenylthio, alkinylthio and cycloalkylthio, or
(b) $R^3$ represents halogen or (in the meaning of "optionally substituted alkoxy") represents alkoxyalkoxyalkoxy,
have now been found.

The compounds of the formula (I) can occur in various stereoisomeric forms where appropriate. The invention relates both to the individual possible stereoisomers and to possible mixtures thereof.

It has furthermore been found that the new N-aryl-nitrogen heterocyclic compounds of the general formula (I) are obtained by a process in which
(a) ketocarboxylic acids of the general formula (II)

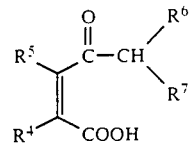

in which $R^4$, $R^5$, $R^6$ and $R^7$ have the abovementioned meanings, are reacted with arylamines of the general formula (III)

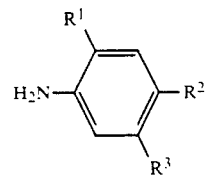

in which $R^1$, $R^2$ and $R^3$ have the abovementioned meanings, if appropriate in the presence of an acidic catalyst and if appropriate in the presence of a diluent, or by a process in which (b) N-aryl-imides of the general formula (IV)

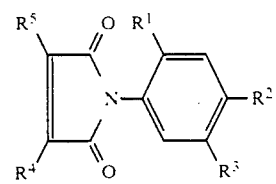

in which $R^1$, $R^2$, $R^3$, $R^4$ and $R^5$ have the abovementioned meanings, are reacted in a first stage with organometallic compounds of the general formula (V)

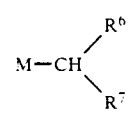

in which
$R^6$ and $R^7$ have the abovementioned meanings and
M represents lithium or the grouping MgX, wherein
X represents chlorine, bromine or iodine, if appropriate in the presence of a diluent, and the hydroxy compounds obtained after treatment with an aqueous acid, of the general formula (VI)

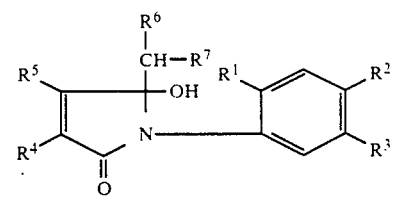

in which $R^1$, $R^2$, $R^3$, $R^4$, $R^5$, $R^6$ and $R^7$ have the abovementioned meanings, are dehydrated in a second stage by customary methods, or by a process in which
(c) in the case where, in formula (I),
$R^3$ represents an optionally substituted radical from the series comprising alkoxy, alkenyloxy, alkinyloxy, cycloalkoxy, alkylthio, alkenylthio, alkinylthio and cycloalkylthio and $R^1$, $R^2$, $R^4$, $R^5$, $R^6$ and $R^7$ have the abovementioned meanings, compounds of the formula (I) in which $R^3$ represents hydroxyl or mercapto and $R^1$, $R^2$, $R^4$, $R^5$, $R^6$ and $R^7$ have the abovementioned meanings, are reacted with alkylating agents of the formula (VII)

$$R^8-X \quad (VII)$$

in which $R^8$ represents in each case optionally substituted alkyl, alkenyl, alkinyl or cycloalkyl and X represents a nucleophilic leaving group, if appropriate in the presence of an acid acceptor and if appropriate in the presence of a diluent, or by a process in which (d) in the case where in formula (I)

$R^3$ represents hydroxyl or mercapto or represents a radical, in each case optionally substituted, from the series comprising alkoxy, alkenyloxy, alkinyloxy, cycloalkoxy, alkylthio, alkenylthio, alkinylthio and cycloalkylthio and $R^1$, $R^2$, $R^4$, $R^5$, $R^6$ and $R^7$ have the abovementioned meanings, compounds of the formula (I) in which $R^3$ represents halogen and $R^1$, $R^2$, $R^4$, $R^5$, $R^6$ and $R^7$ have the abovementioned meanings, are reacted with compounds of the formula (VIII)

$$H\text{-}R^9 \quad (VIII)$$

in which $R^9$ represents hydroxyl or mercapto, or represents an optionally substituted radical from the series comprising alkoxy, alkenyloxy, alkinyloxy, cycloalkoxy, alkylthio, alkenylthio, alkinylthio and cycloalkylthio, or with metal salts of compounds of the formula (VIII) if appropriate in the presence of an acid acceptor and if appropriate in the presence of a diluent.

The new N-aryl-nitrogen heterocyclic compounds of the general formula (I) are distinguished by a potent herbicidal action and can also be employed for regulating plant growth.

The invention preferably relates to compounds of the formula (I) in which $R^1$ represents hydrogen or fluorine, $R^2$ represents cyano, nitro, fluorine, chlorine, bromine, methyl, ethyl, methoxy, ethoxy, methylthio, ethylthio, halogenoalkyl having 1 or 2 carbon atoms and 1 to 5 halogen atoms (in particular fluorine and/or chlorine atoms), halogenoalkoxy having 1 or 2 carbon atoms and 1 to 5 halogen atoms (in particular fluorine and/or chlorine atoms) or halogenoalkylthio having 1 or 2 carbon atoms and 1 to 5 halogen atoms (in particular fluorine and/or chlorine atoms), $R^3$ represents fluorine, chlorine, bromine, hydroxyl or mercapto, or represents in each case optionally substituted straight-chain or branched alkoxy or alkylthio having in each case up to 8 carbon atoms, preferred possible substituents in the alkyl part in each case being: fluorine, chlorine, bromine, cyano, carboxyl, $C_1$-$C_4$-alkoxy, $C_1$-$C_4$-alkoxy-$C_1$-$C_4$-alkoxy, $C_1$-$C_4$-alkylthio, $C_1$-$C_4$-alkyl-carbonyl, $C_1$-$C_4$-alkoxy-carbonyl, $C_3$-$C_6$-cycloalkoxy-carbonyl, $C_3$-$C_6$-cycloalkyl-$C_1$-$C_2$-alkoxy-carbonyl, $C_5$-$C_6$-cycloalkenyloxy-carbonyl, $C_5$-$C_6$-cycloalkenyl-$C_1$-$C_2$-alkoxy-carbonyl and tetrahydrofurylmethoxycarbonyl; or furthermore $R_3$ represents in each case optionally substituted and in each case optionally branched alkenyloxy, alkinyloxy, cycloalkoxy, alkenylthio, alkinylthio or cycloalkylthio having in each case up to 8 carbon atoms, possible substituents in each case being: fluorine, chlorine, bromine, cyano, carboxyl and $C_1$-$C_4$-alkoxy-carbonyl;

$R^4$ represents hydrogen or chlorine, or represents straight-chain or branched alkyl having 1 to 4 carbon atoms, $R^5$ represents hydrogen, chlorine or straight-chain or branched alkyl having 1 to 4 carbon atoms, or $R^5$ together with $R^4$ represents straight-chain or branched alkanediyl having 3 to 6 carbon atoms, $R^6$ represents hydrogen or straight-chain or branched alkyl having 1 to 4 carbon atoms and $R^7$ represents hydrogen or straight-chain or branched alkyl having 1 to 4 carbon atoms, or $R^7$, together with $R^6$, represents straight-chain or branched alkanediyl having 2 to 7 carbon atoms, the abovementioned limitations ("provisos") applying.

The invention particularly relates to compounds of the formula (I) in which $R^1$ represents hydrogen or fluorine, $R^2$ represents cyano, nitro, fluorine, chlorine, bromine, methyl, trifluoromethyl, methoxy, trifluoromethoxy, difluoromethoxy, chlorodifluoromethoxy, methylthio, trifluoromethylthio, difluoromethylthio or chlorodifluoromethylthio, $R^3$ represents fluorine, chlorine, bromine, hydroxyl or mercapto, or represents in each case optionally substituted methoxy, ethoxy, propoxy, isopropoxy, butoxy, isobutoxy, sec-butoxy, tert-butoxy, pentoxy, isopentoxy, sec-pentoxy, tert-pentoxy, hexyloxy, isohexyloxy, methylthio, ethylthio, propylthio, isopropylthio, butylthio, isobutylthio, sec-butylthio, tert-butylthio, pentylthio, isopentylthio, sec-pentylthio, tert-pentylthio, hexylthio or isohexylthio, the optional substituents being fluorine, chlorine, cyano, carboxyl, methoxy, ethoxy, propoxy, isopropoxy, methoxyethoxy, ethoxyethoxy, methylthio, ethylthio, propylthio, isopropylthio, methylcarbonyl, ethylcarbonyl, propylcarbonyl, isopropylcarbonyl, butylcarbonyl, isobutylcarbonyl, sec-butylcarbonyl, tert-butylcarbonyl, methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, cyclopropyloxycarbonyl, cyclopentyloxycarbonyl, cyclohexyloxycarbonyl, cyclopentenyloxycarbonyl, cyclohexenyloxycarbonyl, cyclopropylmethoxycarbonyl, cyclopentylmethoxycarbonyl, cyclohexylmethoxycarbonyl, cyclopentenylmethoxycarbonyl, cyclohexenylmethoxycarbonyl and tetrahydrofurylmethoxycarbonyl; or in which, furthermore, $R^3$ represents allyloxy or 1-methyl-, 2-methyl- or 3-methylallyloxy, or represents propargyloxy or 1-methyl-, 3-methyl- or 1,1-dimethyl-propargyloxy, or represents cyclopropyloxy, cyclopentyloxy or cyclohexyloxy, or represents allylthio or 1-methyl-, 2-methyl- or 3-methyl-allylthio, or represents propargylthio or 1-methyl-, 3-methyl- or 1,1-dimethylpropargylthio, or represents cyclopropylthio, cyclopentylthio or cyclohexylthio, which are in each case optionally substituted by fluorine and/or chlorine;

$R^4$ represents hydrogen, methyl, ethyl, propyl or isopropyl, $R^5$ represents hydrogen, methyl, ethyl, propyl or isopropyl, or together with $R^4$ represents propane1,3- diyl, butane-1,3-diyl, butane-1,4-diyl or 2,2-dimethyl-propane-1,3-diyl,

R⁶ represents hydrogen, methyl, ethyl, propyl, isopropyl, butyl, isobutyl, sec-butyl or tert-butyl and R⁷ represents hydrogen, methyl, ethyl or propyl, or together with R⁶ represents ethane-1,2-diyl, propane1,3-diyl, butane-1,3-diyl, butane-1,4-diyl, pentane1,4-diyl or pentane-1,5-diyl, the abovementioned limitations ("provisos") applying.

Especially preferred compounds of the formula (I) are those in which

R¹ represents hydrogen or fluorine,

R² represents chlorine, cyano or methyl,

R⁴ represents methyl,

R⁵ represents methyl or, together with R⁴, represents —(CH₂)₄—,

R⁶ and R⁷ independently of one another represent hydrogen, methyl or ethyl and

R³ has the meanings mentioned above as preferred or particularly preferred, the abovementioned limitations ("provisos") applying.

Examples of the compounds of the formula (I) are listed in the following Table 1 (compare also the preparation examples):

TABLE 1

Examples of the compounds of the formula (I)

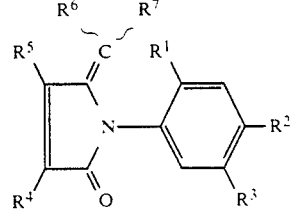

(I)

| R¹ | R² | R³ | R⁴ | R⁵ | R⁶ | R⁷ |
|---|---|---|---|---|---|---|
| H | Cl | SCH₂CH=CH₂ | | —(CH₂)₄— | H | H |
| H | Cl | SCH₂C≡CH | | —(CH₂)₄— | H | H |
| H | Cl | SCH₂COO—⟨C₆H₁₁⟩ | | —(CH₂)₄— | H | H |
| H | Cl | SCH₂COOC₂H₅ | | —(CH₂)₄— | H | H |
| H | Cl | SCHC≡CH<br>\|<br>CH₃ | | —(CH₂)₄— | H | H |
| H | Cl | SCH(CH₃)₂ | | —(CH₂)₄— | H | H |
| H | Cl | SCH(CH₂F)₂ | | —(CH₂)₄— | H | H |
| H | Cl | SCHCOOC₄H₉<br>\|<br>CH₃ | | —(CH₂)₄— | H | H |
| H | Cl | SCH₂CN | | —(CH₂)₄— | H | H |
| H | Cl | SCH₂CH=CHCl | | —(CH₂)₄— | H | H |
| H | Cl | SCH₂CH₂OCH₃ | | —(CH₂)₄— | H | H |
| H | Cl | SCH₂CH₂COOCH₃ | | —(CH₂)₄— | H | H |
| H | Br | SCH₂CH=CH₂ | | —(CH₂)₄— | CH₃ | H |
| H | Br | SCH₂CH=CHCH₃ | | —(CH₂)₄— | CH₃ | H |
| H | Br | SCH₂CH=CHCl | | —(CH₂)₄— | CH₃ | H |
| H | Br | SCH₂C=CH₂<br>\|<br>CH₃ | | —(CH₂)₄— | CH₃ | H |
| H | Br | SCH₂C≡CH | | —(CH₂)₄— | CH₃ | H |
| H | Br | SCH₂C≡CCH₃ | | —(CH₂)₄— | CH₃ | H |
| H | Br | SCH₂COO—⟨C₅H₉⟩ | | —(CH₂)₄— | CH₃ | H |
| H | Br | SCHCOOC₂H₅<br>\|<br>CH₃ | | —(CH₂)₄— | CH₃ | H |
| H | Br | SCH₂COOCH(CH₃)₂ | | —(CH₂)₄— | CH₃ | H |

TABLE 1-continued

Examples of the compounds of the formula (I)

$$\text{(I)}$$

| $R^1$ | $R^2$ | $R^3$ | $R^4$ | $R^5$ | $R^6$ | $R^7$ |
|---|---|---|---|---|---|---|
| H | Br | SCHCOO—⟨cyclohexyl⟩<br>\|<br>CH$_3$ | | —(CH$_2$)$_4$— | CH$_3$ | H |
| H | Br | SCH$_2$COOC$_4$H$_9$ | | —(CH$_2$)$_4$— | CH$_3$ | H |
| F | Br | SCH$_2$CH=CH$_2$ | | —(CH$_2$)$_4$— | CH$_3$ | H |
| F | Br | SCH$_2$CH=CHCH$_3$ | | —(CH$_2$)$_4$— | CH$_3$ | H |
| F | Br | SCH$_2$CH=CHCl | | —(CH$_2$)$_4$— | CH$_3$ | H |
| F | Br | SCH=CH$_2$<br>\|<br>CH$_3$ | | —(CH$_2$)$_4$— | CH$_3$ | H |
| F | Br | SCH$_2$C≡CH | | —(CH$_2$)$_4$— | CH$_3$ | H |
| F | Br | SCH$_2$C≡CCH$_3$ | | —(CH$_2$)$_4$— | CH$_3$ | H |
| F | Br | SCH$_2$COOC$_4$H$_9$ | | —(CH$_2$)$_4$— | CH$_3$ | H |
| F | Br | SCH$_2$COO—⟨cyclopentyl⟩ | | —(CH$_2$)$_4$— | CH$_3$ | H |
| F | Br | SCH—COOC$_2$H$_5$<br>\|<br>CH$_3$ | | —(CH$_2$)$_4$— | CH$_3$ | H |
| H | Br | SCH$_2$CH=CH$_2$ | CH$_3$ | CH$_3$ | H | H |
| H | Br | SCH$_2$CH=CHCH$_3$ | CH$_3$ | CH$_3$ | H | H |
| H | Br | SCH$_2$CH=CHCl | CH$_3$ | CH$_3$ | H | H |
| H | Br | SCH=CH$_2$<br>\|<br>CH$_3$ | CH$_3$ | CH$_3$ | H | H |
| H | Br | SCH$_2$C≡CH | CH$_3$ | CH$_3$ | H | H |
| H | Br | SCH$_2$C≡CCH$_3$ | CH$_3$ | CH$_3$ | H | H |
| H | Br | SCH$_2$COO—⟨cyclopentyl⟩ | CH$_3$ | CH$_3$ | H | H |
| H | Br | SCHCOOC$_2$H$_5$<br>\|<br>CH$_3$ | CH$_3$ | CH$_3$ | H | H |
| H | Br | SCH$_2$COOC$_4$H$_9$ | CH$_3$ | CH$_3$ | H | H |
| F | Br | SCH$_2$CH=CH$_2$ | CH$_3$ | CH$_3$ | H | H |
| F | Br | SCH$_2$CH=CHCH$_3$ | CH$_3$ | CH$_3$ | H | H |
| F | Br | SCH$_2$CH=CHCl | CH$_3$ | CH$_3$ | H | H |
| F | Br | SCH$_2$COOC$_4$H$_9$ | CH$_3$ | CH$_3$ | H | H |
| F | Br | SCHCOOC$_3$H$_7$<br>\|<br>CH$_3$ | CH$_3$ | CH$_3$ | H | H |
| F | Br | SCH$_2$COO—⟨cyclopentyl⟩ | CH$_3$ | CH$_3$ | H | H |

TABLE 1-continued

Examples of the compounds of the formula (I)

$$\text{(I)}$$

| $R^1$ | $R^2$ | $R^3$ | $R^4$ | $R^5$ | $R^6$ | $R^7$ |
|---|---|---|---|---|---|---|
| F | Br | SCH(CH$_3$)COO-cyclopentyl | CH$_3$ | CH$_3$ | H | H |
| F | Br | SCH$_2$C≡CH | CH$_3$ | CH$_3$ | H | H |
| F | Br | SCH$_2$C≡CCH$_3$ | CH$_3$ | CH$_3$ | H | H |
| H | OCF$_3$ | OCH$_2$CH=CH$_2$ | —(CH$_2$)$_4$— | | H | H |
| H | OCF$_3$ | OCH$_2$C≡CH | —(CH$_2$)$_4$— | | H | H |
| H | OCF$_3$ | OCH$_2$COOC$_2$H$_5$ | —(CH$_2$)$_4$— | | H | H |
| H | OCF$_3$ | OCH$_2$CH$_2$OCH$_3$ | —(CH$_2$)$_4$— | | H | H |
| H | SCF$_3$ | OCH$_2$CH=CH$_2$ | —(CH$_2$)$_4$— | | H | H |
| H | SCF$_3$ | OCH$_2$C≡CH | —(CH$_2$)$_4$— | | H | H |
| H | SCF$_3$ | OCH$_2$COOC$_4$H$_9$ | —(CH$_2$)$_4$— | | H | H |
| H | SCF$_3$ | OCH$_2$CH$_2$OC$_2$H$_5$ | —(CH$_2$)$_4$— | | H | H |
| F | OCF$_3$ | OCH$_2$CH=CH$_2$ | —(CH$_2$)$_4$— | | H | H |
| F | OCF$_3$ | OCH$_2$C≡CCH$_3$ | —(CH$_2$)$_4$— | | H | H |
| F | OCF$_3$ | OCH$_2$COO-cyclopentyl | —(CH$_2$)$_4$— | | H | H |
| F | OCF$_3$ | OCH(CH$_3$)COOC$_2$H$_5$ | —(CH$_2$)$_4$— | | H | H |
| F | SCF$_3$ | OCH$_2$CH=CHCl | —(CH$_2$)$_4$— | | H | H |
| F | SCF$_3$ | OCH(CH$_3$)C≡CH | —(CH$_2$)$_4$— | | H | H |
| F | SCF$_3$ | OCH$_2$COOCH(CH$_3$)$_2$ | —(CH$_2$)$_4$— | | H | H |
| F | SCF$_3$ | OCH$_2$CH$_2$SC$_2$H$_5$ | —(CH$_2$)$_4$— | | H | H |
| F | SCF$_3$ | OCH(CH$_3$)COO-cyclopentyl | —(CH$_2$)$_4$— | | H | H |
| H | OCF$_3$ | SCH$_2$CH=CH$_2$ | —(CH$_2$)$_4$— | | H | H |
| H | OCF$_3$ | SCH$_2$COOC$_2$H$_5$ | —(CH$_2$)$_4$— | | H | H |
| H | OCF$_3$ | SCH$_2$C≡CH | —(CH$_2$)$_4$— | | H | H |
| H | OCF$_3$ | SCH$_2$COO-cyclopentyl | —(CH$_2$)$_4$— | | H | H |
| F | OCF$_3$ | SCH$_2$CH=CH$_2$ | —(CH$_2$)$_4$— | | H | H |
| F | OCF$_3$ | SCH$_2$C≡CH | —(CH$_2$)$_4$— | | H | H |
| F | OCF$_3$ | SCH$_2$COO-cyclopentyl | —(CH$_2$)$_4$— | | H | H |
| F | OCF$_3$ | SCH(CH$_3$)COOC$_2$H$_5$ | —(CH$_2$)$_4$— | | H | H |
| H | SCF$_3$ | SCH$_2$CH=CH$_2$ | —(CH$_2$)$_4$— | | H | H |

TABLE 1-continued

Examples of the compounds of the formula (I)

$$\text{(I)}$$

| $R^1$ | $R^2$ | $R^3$ | $R^4$ | $R^5$ | $R^6$ | $R^7$ |
|---|---|---|---|---|---|---|
| H | $SCF_3$ | $SCH_2C\equiv CH$ | | $-(CH_2)_4-$ | H | H |
| H | $SCF_3$ | $SCH_2COOC_2H_5$ | | $-(CH_2)_4-$ | H | H |
| H | $SCF_3$ | $SCH_2CH_2SC_2H_5$ | | $-(CH_2)_4-$ | H | H |
| H | $SCF_3$ | $SCH_2CH_2OC_2H_5$ | | $-(CH_2)_4-$ | H | H |
| F | $SCF_3$ | $SCH_2CH_2SCH_3$ | | $-(CH_2)_4-$ | H | H |
| F | $SCF_3$ | $SCH_2CH=CHCl$ | | $-(CH_2)_4-$ | H | H |
| F | $SCF_3$ | $SCH_2C\equiv CCH_3$ | | $-(CH_2)_4-$ | H | H |
| F | $SCF_3$ | $SCH_2COOC_4H_9$ | | $-(CH_2)_4-$ | H | H |
| F | $SCF_3$ | $SCH_2COO-\text{cyclopentyl}$ | | $-(CH_2)_4-$ | H | H |
| F | $SCF_3$ | $SCHCOOC_2H_5$ \| $CH_3$ | | $-(CH_2)_4-$ | H | H |
| H | $OCHF_2$ | $OCH_2CH=CH_2$ | | $-(CH_2)_4-$ | H | H |
| H | $OCHF_2$ | $OCH_2C\equiv CH$ | | $-(CH_2)_4-$ | H | H |
| H | $OCHF_2$ | $OCH_2COOC_4H_9$ | | $-(CH_2)_4-$ | H | H |
| H | $OCHF_2$ | $OCH_2COO-\text{cyclopentyl}$ | | $-(CH_2)_4-$ | H | H |
| H | $OCHF_2$ | $OCHCOOC_2H_5$ \| $CH_3$ | | $-(CH_2)_4-$ | H | H |
| F | $OCHF_2$ | $OCH_2CH=CH_2$ | | $-(CH_2)_4-$ | H | H |
| F | $OCHF_2$ | $OCH_2C\equiv CCH_3$ | | $-(CH_2)_4-$ | H | H |
| F | $OCHF_2$ | $OCH_2COOC_3H_7$ | | $-(CH_2)_4-$ | H | H |
| F | $OCHF_2$ | $OCH_2COO-\text{cyclopentyl}$ | | $-(CH_2)_4-$ | H | H |
| F | $OCHF_2$ | $OCHCOOCH_3$ \| $CH_3$ | | $-(CH_2)_4-$ | H | H |
| H | $SCHF_2$ | $OCH_2CH=CHCH_3$ | | $-(CH_2)_4-$ | H | H |
| H | $SCHF_2$ | $OCH_2C\equiv CCH_3$ | | $-(CH_2)_4-$ | H | H |
| H | $SCHF_2$ | $OCH_2COO-\text{cyclopentyl}$ | | $-(CH_2)_4-$ | H | H |
| H | $SCHF_2$ | $OCHCOOC_2H_5$ \| $CH_3$ | | $-(CH_2)_4-$ | H | H |
| F | $SCHF_2$ | $OCH_2CH=CHCl$ | | $-(CH_2)_4-$ | H | H |
| F | $SCHF_2$ | $OCH_2C\equiv CH$ | | $-(CH_2)_4-$ | H | H |
| F | $SCHF_2$ | $OCH_2COOC_4H_9$ | | $-(CH_2)_4-$ | H | H |
| F | $SCHF_2$ | $OCHCOOC_2H_5$ \| $CH_3$ | | $-(CH_2)_4-$ | H | H |
| H | $OCHF_2$ | $OCH_2CH=CH_2$ | $CH_3$ | $CH_3$ | $CH_3$ | H |

TABLE 1-continued

Examples of the compounds of the formula (I)

| $R^1$ | $R^2$ | $R^3$ | $R^4$ | $R^5$ | $R^6$ | $R^7$ |
|---|---|---|---|---|---|---|
| H | OCHF$_2$ | SCH$_2$CH=CH$_2$ | | —(CH$_2$)$_4$— | H | H |
| H | OCHF$_2$ | SCH$_2$C≡CH | | —(CH$_2$)$_4$— | H | H |
| H | OCHF$_2$ | SCH$_2$COOC$_4$H$_9$ | | —(CH$_2$)$_4$— | H | H |
| H | OCHF$_2$ | SCHCOOCH$_3$<br>\|<br>CH$_3$ | | —(CH$_2$)$_4$— | H | H |
| F | OCHF$_2$ | SCH$_2$CH=CHCl | | —(CH$_2$)$_4$— | H | H |
| F | OCHF$_2$ | SCH$_2$C≡CCH$_3$ | | —(CH$_2$)$_4$— | H | H |
| F | OCHF$_2$ | SCH$_2$COOC$_3$H$_7$ | | —(CH$_2$)$_4$— | H | H |
| F | OCHF$_2$ | SCH$_2$COO-cyclopentyl | | —(CH$_2$)$_4$— | H | H |
| H | SCHF$_2$ | SCH$_2$CH=CHCH$_3$ | | —(CH$_2$)$_4$— | H | H |
| H | SCHF$_2$ | SCH$_2$C≡CH | | —(CH$_2$)$_4$— | H | H |
| H | SCHF$_2$ | SCH$_2$COOC$_4$H$_9$ | | —(CH$_2$)$_4$— | H | H |
| H | SCHF$_2$ | SCHCOOC$_2$H$_5$<br>\|<br>CH$_3$ | | —(CH$_2$)$_4$— | H | H |
| F | SCHF$_2$ | SCH$_2$CH=CH$_2$ | | —(CH$_2$)$_4$— | H | H |
| F | SCHF$_2$ | SCH$_2$C≡CH | | —(CH$_2$)$_4$— | H | H |
| F | SCHF$_2$ | SCH$_2$CH$_2$SC$_2$H$_5$ | | —(CH$_2$)$_4$— | H | H |
| F | SCHF$_2$ | SCH$_2$CN | | —(CH$_2$)$_4$— | H | H |
| F | SCHF$_2$ | SCH$_2$COOH | | —(CH$_2$)$_4$— | H | H |
| F | SCHF$_2$ | SCHCOOC$_2$H$_5$<br>\|<br>CH$_3$ | | —(CH$_2$)$_4$— | H | H |
| H | CN | OCH$_2$CH=CH$_2$ | | —(CH$_2$)$_4$— | H | H |
| H | CN | OCH$_2$C≡CH | | —(CH$_2$)$_4$— | H | H |
| H | CN | OCH$_2$C≡CCH$_3$ | | —(CH$_2$)$_4$— | H | H |
| H | CN | SCH$_2$CH=CH$_2$ | | —(CH$_2$)$_4$— | H | H |
| H | CN | SCH$_2$CH=CHCH$_3$ | | —(CH$_2$)$_4$— | H | H |
| H | CN | SCH$_2$CH=CHCl | | —(CH$_2$)$_4$— | H | H |
| H | CN | SCH$_2$COOC$_2$H$_5$ | | —(CH$_2$)$_4$— | H | H |
| H | CN | SCHC≡CH<br>\|<br>CH$_3$ | | —(CH$_2$)$_4$— | H | H |
| F | CN | OCH$_2$CH=CHCl | | —(CH$_2$)$_4$— | H | H |
| F | CN | OCH$_2$C≡CH | | —(CH$_2$)$_4$— | H | H |
| F | CN | OCH$_2$C≡CCH$_3$ | | —(CH$_2$)$_4$— | H | H |
| F | CN | OCH$_2$COOC$_4$H$_9$ | | —(CH$_2$)$_4$— | H | H |
| F | CN | OCHC≡CH<br>\|<br>CH$_3$ | | —(CH$_2$)$_4$— | H | H |
| F | CN | SCH$_2$CH=CHCH$_3$ | | —(CH$_2$)$_4$— | H | H |
| F | CN | SCH$_2$C≡CH | | —(CH$_2$)$_4$— | H | H |
| F | CN | SCH$_2$C=CH$_2$<br>\|<br>Cl | | —(CH$_2$)$_4$— | H | H |
| F | CN | SCH$_2$C=CH$_2$<br>\|<br>CH$_3$ | | —(CH$_2$)$_4$— | H | H |

TABLE 1-continued

Examples of the compounds of the formula (I)

$$\text{(I)}$$

| R¹ | R² | R³ | R⁴ | R⁵ | R⁶ | R⁷ |
|----|----|----|----|----|----|----|
| F | CN | SCH₂COO—⟨cyclopentyl⟩ | | —(CH₂)₄— | H | H |
| F | CN | SCH₂COOCH₂—⟨tetrahydrofuryl⟩ | | —(CH₂)₄— | H | H |
| F | CN | SCH₂CN | | —(CH₂)₄— | H | H |
| F | CN | SCH₂CH₂COOC₂H₅ | | —(CH₂)₄— | H | H |
| H | CN | OCH₂C≡CH | | —CH₂CHCH₂CH₂—<br>  \|<br>  CH₃ | H | H |
| F | CN | OCH₂COOC₂H₅ | | —CH₂CHCH₂CH₂—<br>  \|<br>  CH₃ | H | H |
| H | CN | OCH₂CH₂OC₂H₅ | | —CHCH₂CH₂CH₂—<br>  \|<br>  CH₃ | H | H |
| F | CN | SCH₂CH=CHCl | | —CH₂CH₂CHCH₂—<br>  \|<br>  CH₃ | H | H |
| F | CN | SCHC≡CH<br>  \|<br>  CH₃ | | —CH₂CHCH₂CH₂—<br>  \|<br>  CH₃ | H | H |
| H | CN | SCH(CH₂F)₂ | | —CH₂CHCH₂CH₂—<br>  \|<br>  CH₃ | H | H |
| F | CN | SCH₂COO—⟨cyclopentyl⟩ | | —CH₂CHCH₂CH₂—<br>  \|<br>  CH₃ | H | H |
| F | CN | SCH₂CH₂CN | | —CH₂CHCH₂CH₂—<br>  \|<br>  CH₃ | H | H |
| F | CN | O(CH₂CH₂O)₂C₂H₅ | | —CH₂CHCH₂CH₂—<br>  \|<br>  CH₃ | H | H |
| H | CN | O(CH₂CH₂O)₂CH₃ | | —CH₂CHCH₂CH₂—<br>  \|<br>  CH₃ | H | H |
| F | CN | SCH₂CH=CHCl | | —CH₂CHCH₂CH₂—<br>  \|<br>  CH₃ | H | H |
| F | CN | OCHF₂ | | —CH₂CHCH₂CH₂—<br>  \|<br>  CH₃ | H | H |

TABLE 1-continued

Examples of the compounds of the formula (I)

| $R^1$ | $R^2$ | $R^3$ | $R^4$ | $R^5$ | $R^6$ | $R^7$ |
|---|---|---|---|---|---|---|
| H | Cl | $SCH_2CH=CH_2$ | $-CH_2CH(CH_3)CH_2CH_2-$ | H | H | |
| H | Cl | $SCH_2C\equiv CH$ | $-CH_2CH(CH_3)CH_2CH_2-$ | H | H | |
| H | Cl | $SCH_2COOC_4H_9$ | $-CH_2CH(CH_3)CH_2CH_2-$ | H | H | |
| F | CN | $OCH_2CH=CHCH_3$ | $-(CH_2)_4-$ | $CH_3$ | H | |
| F | CN | $OCH_2C\equiv CH$ | $-(CH_2)_4-$ | $CH_3$ | H | |
| F | CN | $OCH_2CH_2OC_2H_5$ | $-(CH_2)_4-$ | $CH_3$ | H | |
| F | CN | $OCH_2COOC_3H_7$ | $-(CH_2)_4-$ | $CH_3$ | H | |
| F | CN | $OCH_2COO$-cyclopentyl | $-(CH_2)_4-$ | $CH_3$ | H | |
| F | CN | $OCH(CH_3)COOC_2H_5$ | $-(CH_2)_4-$ | $CH_3$ | H | |
| F | CN | $SCH_2CH\equiv CH$ | $-(CH_2)_4-$ | $CH_3$ | H | |
| F | CN | $SCH(CH_3)C\equiv CH$ | $-(CH_2)_4-$ | $CH_3$ | H | |
| F | CN | $SCH_2CH=CHCl$ | $-(CH_2)_4-$ | $CH_3$ | H | |
| F | CN | $SCH_2COOCH(CH_3)_2$ | $-(CH_2)_4-$ | $CH_3$ | H | |
| F | CN | $SCH_2COO$-cyclopentyl | $-(CH_2)_4-$ | $CH_3$ | H | |
| F | CN | $SCH(CH_3)CN$ | $-(CH_2)_4-$ | $CH_3$ | H | |
| F | CN | $SCH_2CH_2SCH_3$ | $-(CH_2)_4-$ | $CH_3$ | H | |
| F | CN | $SCH(CH_3)COOCH_3$ | $-(CH_2)_4-$ | $CH_3$ | H | |
| H | CN | $OCH_2C\equiv CH$ | $-(CH_2)_4-$ | $CH_3$ | H | |
| H | CN | $OCH_2CH=CHCl$ | $-(CH_2)_4-$ | $CH_3$ | H | |
| H | CN | $OCH_2COOC_4H_9$ | $-(CH_2)_4-$ | $CH_3$ | H | |
| H | CN | $O(CH_2CH_2O)_2C_2H_5$ | $-(CH_2)_4-$ | $CH_3$ | H | |
| H | CN | $OCH(CH_3)COOC_2H_5$ | $-(CH_2)_4-$ | $CH_3$ | H | |
| H | CN | $SCH_2C\equiv CCH_3$ | $-(CH_2)_4-$ | $CH_3$ | H | |
| H | CN | $SCH_2CH=CHCH_3$ | $-(CH_2)_4-$ | $CH_3$ | H | |

TABLE 1-continued

Examples of the compounds of the formula (I)

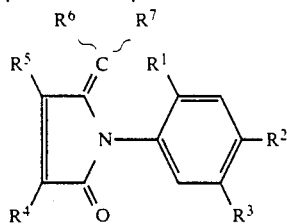

(I)

| $R^1$ | $R^2$ | $R^3$ | $R^4$ | $R^5$ | $R^6$ | $R^7$ |
|---|---|---|---|---|---|---|
| H | CN | SCH$_2$COO—⟨cyclopentyl⟩ | | —(CH$_2$)$_4$— | CH$_3$ | H |
| H | CN | SCH(CH$_2$F)$_2$ | | —(CH$_2$)$_4$— | CH$_3$ | H |
| H | CN | SCH$_2$CH$_2$CN | | —(CH$_2$)$_4$— | CH$_3$ | H |
| H | Cl | SCH$_2$CH=CH$_2$ | | —(CH$_2$)$_4$— | CH$_3$ | H |
| H | Cl | SCH$_2$C≡CCH$_3$ | | —(CH$_2$)$_4$— | CH$_3$ | H |
| H | Cl | SCHC≡CH, CH$_3$ | | —(CH$_2$)$_4$— | CH$_3$ | H |
| H | Cl | SCH$_2$COO—⟨cyclopentyl⟩ | | —(CH$_2$)$_4$— | CH$_3$ | H |
| H | Cl | SCH(CH$_2$F)$_2$ | | —(CH$_2$)$_4$— | CH$_3$ | H |
| H | Cl | SCH$_2$COOC$_4$H$_9$ | | —(CH$_2$)$_4$— | CH$_3$ | H |
| H | Cl | SCH$_2$CN | | —(CH$_2$)$_4$— | CH$_3$ | H |
| H | Cl | SCH$_2$CH$_2$SCH$_3$ | | —(CH$_2$)$_4$— | CH$_3$ | H |
| H | Cl | SCHCOOC$_2$H$_5$, CH$_3$ | | —(CH$_2$)$_4$— | CH$_3$ | H |
| F | Cl | SCH$_2$CH=CH$_2$ | | —(CH$_2$)$_4$— | CH$_3$ | H |
| F | Cl | SCH$_2$C≡CH | | —(CH$_2$)$_4$— | CH$_3$ | H |
| F | Cl | SCHC≡CH, CH$_3$ | | —(CH$_2$)$_4$— | CH$_3$ | H |
| F | Cl | SCH$_2$COOC$_4$H$_9$ | | —(CH$_2$)$_4$— | CH$_3$ | H |
| F | Cl | SCHCOOC$_2$H$_5$, CH$_3$ | | —(CH$_2$)$_4$— | CH$_3$ | H |
| F | CN | SCH$_2$CH=CHCH$_3$ | | —(CH$_2$)$_4$— | CH$_3$ | H |
| F | CN | SCH$_2$C≡CCH$_3$ | | —(CH$_2$)$_4$— | CH$_3$ | H |
| F | CN | SCH$_2$COOC$_3$H$_7$ | | —(CH$_2$)$_4$— | CH$_3$ | H |
| F | CN | SCH(CH$_2$F)$_2$ | | —(CH$_2$)$_4$— | CH$_3$ | H |
| F | CN | SCHCOOCH$_3$, CH$_3$ | | —(CH$_2$)$_4$— | CH$_3$ | H |
| F | CN | OCH$_2$CH=CH$_2$ | | —(CH$_2$)$_4$— | CH$_3$ | H |
| F | CN | OCH$_2$C≡CH | | —(CH$_2$)$_4$— | CH$_3$ | H |
| F | CN | OCHF$_2$ | | —(CH$_2$)$_4$— | CH$_3$ | H |
| F | CN | OCF$_2$CHF$_2$ | | —(CH$_2$)$_4$— | CH$_3$ | H |
| F | CN | OCHFCF$_3$ | | —(CH$_2$)$_4$— | CH$_3$ | H |
| F | CN | OCF$_2$CHFCl | | —(CH$_2$)$_4$— | CH$_3$ | H |
| F | CN | OCH$_2$CH$_2$OC$_2$H$_5$ | | —(CH$_2$)$_4$— | CH$_3$ | H |
| F | CN | OCH$_2$COOC$_4$H$_9$ | | —(CH$_2$)$_4$— | CH$_3$ | H |
| F | CN | OCH$_2$COO—⟨cyclopentyl⟩ | | —(CH$_2$)$_4$— | CH$_3$ | H |

TABLE 1-continued

Examples of the compounds of the formula (I)

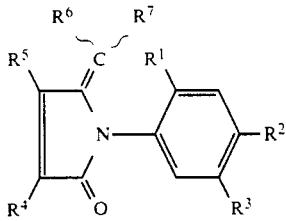

(I)

| $R^1$ | $R^2$ | $R^3$ | $R^4$ | $R^5$ | $R^6$ | $R^7$ |
|---|---|---|---|---|---|---|
| F | CN | OCHCOOC$_2$H$_5$ \| CH$_3$ | | —(CH$_2$)$_4$— | CH$_3$ | H |
| H | CN | OCH$_2$CH=CHCl | | —(CH$_2$)$_4$— | CH$_3$ | H |
| H | CN | OCH$_2$C≡CH | | —(CH$_2$)$_4$— | CH$_3$ | H |
| H | CN | OCH$_2$COOC$_3$H$_7$ | | —(CH$_2$)$_4$— | CH$_3$ | H |
| H | CN | O(CH$_2$CH$_2$O)$_2$CH$_3$ | | —(CH$_2$)$_4$— | CH$_3$ | H |
| H | CN | SCH$_2$CN | | —(CH$_2$)$_4$— | CH$_3$ | H |
| H | CN | SCH$_2$C≡CH | | —(CH$_2$)$_4$— | CH$_3$ | H |
| H | CN | SCH$_2$COO—⟨cyclopentyl⟩ | | —(CH$_2$)$_4$— | CH$_3$ | H |
| F | Cl | SCH$_2$CH=CH$_2$ | | —(CH$_2$)$_4$— | CH$_3$ | H |
| F | Cl | SCH$_2$CH=CHCl | | —(CH$_2$)$_4$— | CH$_3$ | H |
| F | Cl | SCH$_2$CH=CHCH$_3$ | | —(CH$_2$)$_4$— | CH$_3$ | H |
| F | Cl | SCH$_2$C≡CH | | —(CH$_2$)$_4$— | CH$_3$ | H |
| F | Cl | SCH$_2$C≡CCH$_3$ | | —(CH$_2$)$_4$— | CH$_3$ | H |
| F | Cl | SCH$_2$CH$_2$SCH$_3$ | | —(CH$_2$)$_4$— | CH$_3$ | H |
| F | Cl | SCH$_2$COOC$_3$H$_7$ | | —(CH$_2$)$_4$— | CH$_3$ | H |
| F | Cl | SCH$_2$COO—⟨cyclopentyl⟩ | | —(CH$_2$)$_4$— | CH$_3$ | H |
| F | Cl | SCH$_2$COOCH$_2$—⟨tetrahydrofuranyl⟩ | | —(CH$_2$)$_4$— | CH$_3$ | H |
| F | Cl | SCH$_2$CH$_2$COOCH$_3$ | | —(CH$_2$)$_4$— | CH$_3$ | H |
| F | Cl | SCH(CH$_2$F)$_2$ | | —(CH$_2$)$_4$— | CH$_3$ | H |
| F | CN | OCH$_2$CH=CH$_2$ | | —(CH$_2$)$_4$— | C$_2$H$_5$ | H |
| F | CN | OCH$_2$C≡CH | | —(CH$_2$)$_4$— | C$_2$H$_5$ | H |
| F | CN | OCH$_2$COOC$_3$H$_7$ | | —(CH$_2$)$_4$— | C$_2$H$_5$ | H |
| F | CN | OCH$_2$CH$_2$OC$_2$H$_5$ | | —(CH$_2$)$_4$— | C$_2$H$_5$ | H |
| F | CN | O(CH$_2$CH$_2$O)$_2$C$_2$H$_5$ | | —(CH$_2$)$_4$— | C$_2$H$_5$ | H |
| F | CN | OCHF$_2$ | | —(CH$_2$)$_4$— | C$_2$H$_5$ | H |
| F | CN | SCH$_2$CH=CH$_2$ | | —(CH$_2$)$_4$— | C$_2$H$_5$ | H |
| F | CN | SCH$_2$C≡CH | | —(CH$_2$)$_4$— | C$_2$H$_5$ | H |
| F | CN | SCH$_2$C≡CCH$_3$ | | —(CH$_2$)$_4$— | C$_2$H$_5$ | H |
| F | CN | SCHC≡CH \| CH$_3$ | | —(CH$_2$)$_4$— | C$_2$H$_5$ | H |
| F | CN | SCH$_2$CH=CHCl | | —(CH$_2$)$_4$— | C$_2$H$_5$ | H |
| F | CN | SCH$_2$COOC$_4$H$_9$ | | —(CH$_2$)$_4$— | C$_2$H$_5$ | H |
| F | CN | SCH$_2$COO—⟨cyclopentyl⟩ | | —(CH$_2$)$_4$— | C$_2$H$_5$ | H |
| F | CN | SCHCOOCH$_3$ \| CH$_3$ | | —(CH$_2$)$_4$— | C$_2$H$_5$ | H |
| F | CN | SCH(CH$_2$F)$_2$ | | —(CH$_2$)$_4$— | C$_2$H$_5$ | H |
| F | CN | SCH$_2$CH$_2$CN | | —(CH$_2$)$_4$— | C$_2$H$_5$ | H |

TABLE 1-continued

Examples of the compounds of the formula (I)

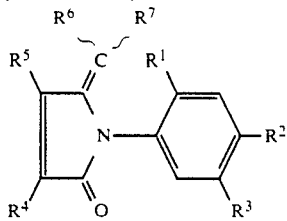

(I)

| R¹ | R² | R³ | R⁴ | R⁵ | R⁶ | R⁷ |
|----|----|----|----|----|----|----|
| F | CN | SCH₂COOCH₂-(tetrahydrofuran-2-yl) | | —(CH₂)₄— | C₂H₅ | H |
| H | CN | OCH₂COOC₄H₉ | | —(CH₂)₄— | C₂H₅ | H |
| H | CN | OCH₂C≡CH | | —(CH₂)₄— | C₂H₅ | H |
| H | CN | SCH₂COO-(cyclopentyl) | | —(CH₂)₄— | C₂H₅ | H |
| H | CN | SCHCOOC₂H₅ \| CH₃ | | —(CH₂)₄— | C₂H₅ | H |
| H | CN | OCHF₂ | | —(CH₂)₄— | C₂H₅ | H |
| H | CN | O(CH₂CH₂O)₂C₂H₅ | | —(CH₂)₄— | C₂H₅ | H |
| H | CN | SCH₂CH₂COOCH₃ | | —(CH₂)₄— | C₂H₅ | H |
| H | CN | SCH₂C≡CCH₃ | | —(CH₂)₄— | C₂H₅ | H |
| H | Cl | SCH₂CH=CH₂ | | —(CH₂)₄— | C₂H₅ | H |
| H | Cl | SCH₂CH=CHCl | | —(CH₂)₄— | C₂H₅ | H |
| H | Cl | SCH₂CH=CHCH₃ | | —(CH₂)₄— | C₂H₅ | H |
| H | Cl | SCH₂C=CH₂ \| Cl | | —(CH₂)₄— | C₂H₅ | H |
| H | Cl | SCHCH=CH₂ \| CH₃ | | —(CH₂)₄— | C₂H₅ | H |
| H | Cl | SCH₂COOC₂H₅ | | —(CH₂)₄— | C₂H₅ | H |
| H | Cl | SCH(CH₂F)₂ | | —(CH₂)₄— | C₂H₅ | H |
| H | Cl | SCH₂COO-(cyclopentyl) | | —(CH₂)₄— | C₂H₅ | H |
| H | Cl | SCHCOOC₂H₅ \| CH₃ | | —(CH₂)₄— | C₂H₅ | H |
| H | Cl | SCH₂CH₂CN | | —(CH₂)₄— | C₂H₅ | H |
| H | Cl | SCH₂CH₂COOCH₃ | | —(CH₂)₄— | C₂H₅ | H |
| F | Cl | SCH₂CH=CH₂ | | —(CH₂)₄— | C₂H₅ | H |
| F | Cl | SCH₂C≡CH | | —(CH₂)₄— | C₂H₅ | H |
| F | Cl | SCH₂COOC₄H₉ | | —(CH₂)₄— | C₂H₅ | H |
| F | Cl | SCH₂CH₂COOCH₃ | | —(CH₂)₄— | C₂H₅ | H |
| F | Cl | SCH₂COO-(cyclopentyl) | | —(CH₂)₄— | C₂H₅ | H |
| F | Cl | SCHCOOCH₃ \| CH₃ | | —(CH₂)₄— | C₂H₅ | H |
| F | CN | OCH₂CH=CH₂ | | —(CH₂)₄— | C₃H₇ | H |
| F | CN | OCH₂C≡CH | | —(CH₂)₄— | C₃H₇ | H |
| F | CN | OCH₂COOC₂H₅ | | —(CH₂)₄— | C₃H₇ | H |

TABLE 1-continued

Examples of the compounds of the formula (I)

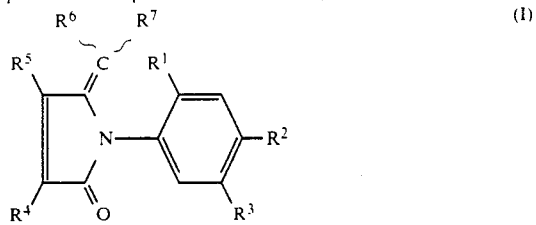

(I)

| $R^1$ | $R^2$ | $R^3$ | $R^4$ | $R^5$ | $R^6$ | $R^7$ |
|---|---|---|---|---|---|---|
| F | CN | OCH₂COO—⟨cyclopentyl⟩ | | —(CH₂)₄— | C₃H₇ | H |
| F | CN | SCHCH=CH₂<br>\|<br>CH₃ | | —(CH₂)₄— | C₃H₇ | H |
| F | CN | SCH₂CH=CHCl | | —(CH₂)₄— | C₃H₇ | H |
| F | CN | SCH₂COOC₄H₉ | | —(CH₂)₄— | C₃H₇ | H |
| F | CN | SCHCOOC₂H₅<br>\|<br>CH₃ | | —(CH₂)₄— | C₃H₇ | H |
| F | CN | SCH₂CH₂COOCH₃ | | —(CH₂)₄— | C₃H₇ | H |
| F | CN | SCH(CH₂F)₂ | | —(CH₂)₄— | C₃H₇ | H |
| H | CN | OCH₂CH=CHCH₃ | | —(CH₂)₄— | C₃H₇ | H |
| H | CN | OCH₂CH=CHCl | | —(CH₂)₄— | C₃H₇ | H |
| H | CN | OCH₂C≡CCH₃ | | —(CH₂)₄— | C₃H₇ | H |
| H | CN | OCH₂COOC₄H₉ | | —(CH₂)₄— | C₃H₇ | H |
| H | CN | OCH₂COOCH₂—⟨tetrahydrofuranyl⟩ | | —(CH₂)₄— | C₃H₇ | H |
| H | CN | SCH₂C≡CH | | —(CH₂)₄— | C₃H₇ | H |
| H | CN | —CH₂CH₂CHCH₂—<br>\|<br>CH₃ | | —(CH₂)₄— | C₃H₇ | H |
| H | CN | SCH₂COOC₃H₇ | | —(CH₂)₄— | C₃H₇ | H |
| H | CN | SCH₂CH₂CN | | —(CH₂)₄— | C₃H₇ | H |
| H | CN | SCH₂CH₂COOC₂H₅ | | —(CH₂)₄— | C₃H₇ | H |
| H | CN | SCHCOOC₂H₅<br>\|<br>CH₃ | | —(CH₂)₄— | C₃H₇ | H |
| H | Cl | SCH₂CH=CH₂ | | —(CH₂)₄— | C₃H₇ | H |
| H | Cl | SCH₂CH=CHCl | | —(CH₂)₄— | C₃H₇ | H |
| H | Cl | SCH₂C=CH₂<br>\|<br>Cl | | —(CH₂)₄— | C₃H₇ | H |
| H | Cl | SCH₂C≡CH | | —(CH₂)₄— | C₃H₇ | H |
| H | Cl | SCH₂C≡CCH₃ | | —(CH₂)₄— | C₃H₇ | H |
| H | Cl | SCHC≡CH<br>\|<br>CH₃ | | —(CH₂)₄— | C₃H₇ | H |
| H | Cl | SCH₂COOC₄H₉ | | —(CH₂)₄— | C₃H₇ | H |
| H | Cl | SCH₂COO—⟨cyclopentyl⟩ | | —(CH₂)₄— | C₃H₇ | H |
| H | Cl | SCHCOOCH₃<br>\|<br>CH₃ | | —(CH₂)₄— | C₃H₇ | H |

TABLE 1-continued

Examples of the compounds of the formula (I)

$$\text{(I)}$$

Structure: A pyrrolinone ring with R⁵ and R⁴ on ring carbons, =C(R⁶)(R⁷) exocyclic double bond, N substituted with a phenyl group bearing R¹ (ortho), R² (para), R³ (meta).

| R¹ | R² | R³ | R⁴ | R⁵ | R⁶ | R⁷ |
|---|---|---|---|---|---|---|
| F | Cl | SCH₂CH=CH₂ | | —(CH₂)₄— | C₃H₇ | H |
| F | Cl | SCH₂CH=CHCH₃ | | —(CH₂)₄— | C₃H₇ | H |
| F | Cl | SCH₂C≡CH | | —(CH₂)₄— | C₃H₇ | H |
| F | Cl | SCH(CH₃)C≡CH | | —(CH₂)₄— | C₃H₇ | H |
| F | Cl | SCH₂COOC₃H₇ | | —(CH₂)₄— | C₃H₇ | H |
| F | Cl | SCH₂COOCH₂-(tetrahydrofuran-2-yl) | | —(CH₂)₄— | C₃H₇ | H |
| F | Cl | SCH₂CH₂CN | | —(CH₂)₄— | C₃H₇ | H |
| F | Cl | SCH₂CH₂COOC₂H₅ | | —(CH₂)₄— | C₃H₇ | H |
| F | Cl | SCH(CH₃)COOCH₃ | | —(CH₂)₄— | C₃H₇ | H |
| F | CN | OCH₂CH=CH₂ | | —(CH₂)₄— | CH₃ | CH₃ |
| F | CN | OCH₂C≡CH | | —(CH₂)₄— | CH₃ | CH₃ |
| F | CN | OCH₂COOC₂H₅ | | —(CH₂)₄— | CH₃ | CH₃ |
| F | CN | OCH(CH₂F)₂ | | —(CH₂)₄— | CH₃ | CH₃ |
| F | CN | SCH₂CH=CH₂ | | —(CH₂)₄— | CH₃ | CH₃ |
| F | CN | SCH(CH₃)C≡CH | | —(CH₂)₄— | CH₃ | CH₃ |
| F | CN | SCH₂C≡CCH₃ | | —(CH₂)₄— | CH₃ | CH₃ |
| F | CN | SCH₂COOC₄H₉ | | —(CH₂)₄— | CH₃ | CH₃ |
| F | CN | SCH₂CH₂CN | | —(CH₂)₄— | CH₃ | CH₃ |
| F | CN | SCH₂CH₂COOCH₃ | | —(CH₂)₄— | CH₃ | CH₃ |
| F | CN | SCH(CH₃)COOC₂H₅ | | —(CH₂)₄— | CH₃ | CH₃ |
| H | CN | OCH₂CH=CHCH₃ | | —(CH₂)₄— | CH₃ | CH₃ |
| H | CN | OCH₂CH=CH₂ | | —(CH₂)₄— | CH₃ | CH₃ |
| H | CN | OCH₂C≡CH | | —(CH₂)₄— | CH₃ | CH₃ |
| H | CN | OCHF₂ | | —(CH₂)₄— | CH₃ | CH₃ |
| H | CN | OCH(CH₂F)₂ | | —(CH₂)₄— | CH₃ | CH₃ |
| H | CN | OCH₂COOC₄H₉ | | —(CH₂)₄— | CH₃ | CH₃ |
| H | CN | SCH₂CH=CH₂ | | —(CH₂)₄— | CH₃ | CH₃ |
| H | CN | SCH₂C≡CH | | —(CH₂)₄— | CH₃ | CH₃ |
| H | CN | SCH₂COOC₂H₅ | | —(CH₂)₄— | CH₃ | CH₃ |
| H | CN | SCH(CH₃)COOCH₃ | | —(CH₂)₄— | CH₃ | CH₃ |
| H | Cl | SCH₂CH=CH₂ | | —(CH₂)₄— | CH₃ | CH₃ |
| H | Cl | SCH₂C≡CH | | —(CH₂)₄— | CH₃ | CH₃ |
| H | Cl | SC(CH₃)₂C≡CH | | —(CH₂)₄— | CH₃ | CH₃ |
| H | Cl | SCH₂COOC₂H₅ | | —(CH₂)₄— | CH₃ | CH₃ |
| H | Cl | SCH₂CH₂CN | | —(CH₂)₄— | CH₃ | CH₃ |
| H | Cl | SCH₂CH₂COOCH₃ | | —(CH₂)₄— | CH₃ | CH₃ |

TABLE 1-continued

| | | | | | | |
|---|---|---|---|---|---|---|
| H | Cl | SCHCOOC$_2$H$_5$<br>\|<br>CH$_3$ | | —(CH$_2$)$_4$— | CH$_3$ | CH$_3$ |
| F | Cl | SCH$_2$CH=CHCH$_3$ | | —(CH$_2$)$_4$— | CH$_3$ | CH$_3$ |
| F | Cl | SCH$_2$C≡CH | | —(CH$_2$)$_4$— | CH$_3$ | CH$_3$ |
| F | Cl | SCH$_2$CH=CHCl | | —(CH$_2$)$_4$— | CH$_3$ | CH$_3$ |
| F | Cl | SCH$_2$C=CH$_2$<br>\|<br>Cl | | —(CH$_2$)$_4$— | CH$_3$ | CH$_3$ |
| F | Cl | SCHC≡CH<br>\|<br>CH$_3$ | | —(CH$_2$)$_4$— | CH$_3$ | CH$_3$ |
| F | Cl | SCH$_2$COOC$_2$H$_5$ | | —(CH$_2$)$_4$— | CH$_3$ | CH$_3$ |
| F | Cl | SCH$_2$COO—⬠ | | —(CH$_2$)$_4$— | CH$_3$ | CH$_3$ |
| F | Cl | SCHCOOCH$_3$<br>\|<br>CH$_3$ | | —(CH$_2$)$_4$— | CH$_3$ | CH$_3$ |
| F | Cl | SCH(CH$_2$F)$_2$ | | —(CH$_2$)$_4$— | CH$_3$ | CH$_3$ |
| F | Cl | SCH$_2$CH$_2$CN | | —(CH$_2$)$_4$— | CH$_3$ | CH$_3$ |
| F | Cl | SCH$_2$CH$_2$COOCH$_3$ | | —(CH$_2$)$_4$— | CH$_3$ | CH$_3$ |
| F | CN | OCH$_2$CH=CH$_2$ | CH$_3$ | CH$_3$ | H | H |
| F | CN | OCH$_2$C≡CH | CH$_3$ | CH$_3$ | H | H |
| F | CN | OCHF$_2$ | CH$_3$ | CH$_3$ | H | H |
| F | CN | OCH(CH$_2$F)$_2$ | CH$_3$ | CH$_3$ | H | H |
| F | CN | OCF$_2$CHFCl | CH$_3$ | CH$_3$ | H | H |
| F | CN | OCH$_2$COOC$_4$H$_9$ | CH$_3$ | CH$_3$ | H | H |
| F | CN | SCH$_2$CH=CH$_3$ | CH$_3$ | CH$_3$ | H | H |
| F | CN | SCH$_2$C≡CH | CH$_3$ | CH$_3$ | H | H |
| F | CN | SCHC≡CH<br>\|<br>CH$_3$ | CH$_3$ | CH$_3$ | H | H |
| F | CN | SCH$_2$CN | CH$_3$ | CH$_3$ | H | H |
| F | CN | SCH$_2$CH$_2$CN | CH$_3$ | CH$_3$ | H | H |
| F | CN | SCH$_2$COOC$_3$H$_7$ | CH$_3$ | CH$_3$ | H | H |
| F | CN | SCH$_2$COO—⬠ | CH$_3$ | CH$_3$ | H | H |
| H | CN | OCH$_2$CH=CHCH$_3$ | CH$_3$ | CH$_3$ | H | H |
| H | CN | OCH$_2$C≡CCH$_3$ | CH$_3$ | CH$_3$ | H | H |
| H | CN | OCH$_2$COOC$_4$H$_9$ | CH$_3$ | CH$_3$ | H | H |
| H | CN | SCH$_2$C≡CH | CH$_3$ | CH$_3$ | H | H |
| H | CN | SCHC≡CH<br>\|<br>CH$_3$ | CH$_3$ | CH$_3$ | H | H |
| H | CN | SCH$_2$COOC$_3$H$_7$ | CH$_3$ | CH$_3$ | H | H |
| H | CN | SCH$_2$CH$_2$COOCH$_3$ | CH$_3$ | CH$_3$ | H | H |
| H | CN | SCHCOOCH$_3$<br>\|<br>CH$_3$ | CH$_3$ | CH$_3$ | H | H |
| H | Cl | SCH$_2$CH=CH$_2$ | CH$_3$ | CH$_3$ | H | H |
| H | Cl | SCHCH=CH$_2$<br>\|<br>CH$_3$ | CH$_3$ | CH$_3$ | H | H |
| H | Cl | SCH$_2$CH=CHCl | CH$_3$ | CH$_3$ | H | H |
| H | Cl | SCH$_2$C≡CH | CH$_3$ | CH$_3$ | H | H |
| H | Cl | SC(CH$_3$)$_2$C≡CH | CH$_3$ | CH$_3$ | H | H |
| H | Cl | SCH$_2$COOC$_3$H$_7$ | CH$_3$ | CH$_3$ | H | H |

TABLE 1-continued

| | | | | | | |
|---|---|---|---|---|---|---|
| H | Cl | SCH₂COO—⟨cyclopentyl⟩ | CH₃ | CH₃ | H | H |
| H | Cl | SCH₂CH₂CN | CH₃ | CH₃ | H | H |
| H | Cl | SCH₂CH₂COOCH₃ | CH₃ | CH₃ | H | H |
| H | Cl | SCHCOOCH₃<br>\|<br>CH₃ | CH₃ | CH₃ | H | H |
| F | Cl | SCH₂CH=CH₂ | CH₃ | CH₃ | H | H |
| F | Cl | SCH₂C=CH₂<br>\|<br>Cl | CH₃ | CH₃ | H | H |
| F | Cl | SCH₂C≡CH | CH₃ | CH₃ | H | H |
| F | Cl | SCHC≡CH<br>\|<br>CH₃ | CH₃ | CH₃ | H | H |
| F | Cl | SCH₂CH₂CN | CH₃ | CH₃ | H | H |
| F | Cl | SCH₂CH₂COOCH₃ | CH₃ | CH₃ | H | H |
| F | Cl | SCH₂COOC₂H₅ | CH₃ | CH₃ | H | H |
| F | Cl | SCH(CH₂F)₂ | CH₃ | CH₃ | H | H |
| F | Cl | SCHCOOCH₃<br>\|<br>CH₃ | CH₃ | CH₃ | H | H |
| F | CN | OCH₂CH=CH₂ | CH₃ | CH₃ | CH₃ | H |
| F | CN | OCH₂C≡CH | CH₃ | CH₃ | CH₃ | H |
| F | CN | OCH₂COOC₂H₅ | CH₃ | CH₃ | CH₃ | |
| F | CN | O(CH₂CH₂O)₂C₂H₅ | CH₃ | CH₃ | CH₃ | H |
| F | CN | OCHCOOCH₃<br>\|<br>CH₃ | CH₃ | CH₃ | CH₃ | H |
| F | CN | SCH₂CH=CHCl | CH₃ | CH₃ | CH₃ | H |
| F | CN | SCH₂C≡CCH₃ | CH₃ | CH₃ | CH₃ | H |
| F | CN | SCH₂CH₂CN | CH₃ | CH₃ | CH₃ | H |
| F | CN | SCH(CH₂F)₂ | CH₃ | CH₃ | CH₃ | H |
| F | CN | SCH₂COOC₃H₇ | CH₃ | CH₃ | CH₃ | H |
| F | CN | SCHCOOC₂H₅<br>\|<br>CH₃ | CH₃ | CH₃ | CH₃ | H |
| H | CN | OCH₂CH=CHCH₃ | CH₃ | CH₃ | CH₃ | H |
| H | CN | OCH₂C≡CH | CH₃ | CH₃ | CH₃ | H |
| H | CN | OCHC≡CH<br>\|<br>CH₃ | CH₃ | CH₃ | CH₃ | H |
| H | CN | OCH₂COOC₄H₉ | CH₃ | CH₃ | CH₃ | H |
| H | CN | OCHCOOC₂H₅<br>\|<br>CH₃ | CH₃ | CH₃ | CH₃ | H |
| H | CN | SCH₂CH=CHCl | CH₃ | CH₃ | CH₃ | H |
| H | CN | SCH₂C≡CH | CH₃ | CH₃ | CH₃ | H |
| H | CN | SC(CH₃)₂C≡CH | CH₃ | CH₃ | CH₃ | H |
| H | CN | SCH₂COOC₂H₅ | CH₃ | CH₃ | CH₃ | H |
| H | CN | SCHCOOCH₃<br>\|<br>CH₃ | CH₃ | CH₃ | CH₃ | H |
| H | Cl | SCH₂CH=CH₂ | CH₃ | CH₃ | CH₃ | H |
| H | Cl | SCHCH=CH₂<br>\|<br>CH₃ | CH₃ | CH₃ | CH₃ | H |

TABLE 1-continued

| | | | | | | |
|---|---|---|---|---|---|---|
| H | Cl | SCH$_2$C≡CH | CH$_3$ | CH$_3$ | CH$_3$ | H |
| H | Cl | SC(CH$_3$)$_2$C≡CH | CH$_3$ | CH$_3$ | CH$_3$ | H |
| H | Cl | SCH$_2$C≡CCH$_3$ | CH$_3$ | CH$_3$ | CH$_3$ | H |
| H | Cl | SCH$_2$COOC$_3$H$_7$ | CH$_3$ | CH$_3$ | CH$_3$ | H |
| H | Cl | SCHCOOC$_2$H$_5$ \| CH$_3$ | CH$_3$ | CH$_3$ | CH$_3$ | H |
| F | Cl | SCH$_2$CH=CH$_2$ | CH$_3$ | CH$_3$ | CH$_3$ | H |
| F | Cl | SCH$_2$CH=CHCH$_3$ | CH$_3$ | CH$_3$ | CH$_3$ | H |
| F | Cl | SCH$_2$CH=CHCl | CH$_3$ | CH$_3$ | CH$_3$ | H |
| F | Cl | SCH$_2$C≡CH | CH$_3$ | CH$_3$ | CH$_3$ | H |
| F | Cl | SCHC≡CH \| CH$_3$ | CH$_3$ | CH$_3$ | CH$_3$ | H |
| F | Cl | SCH$_2$C≡CCH$_3$ | CH$_3$ | CH$_3$ | CH$_3$ | H |
| F | Cl | SCH$_2$CH$_2$CN | CH$_3$ | CH$_3$ | CH$_3$ | H |
| F | Cl | SCH$_2$CH$_2$COOCH$_3$ | CH$_3$ | CH$_3$ | CH$_3$ | H |
| F | Cl | SCH(CH$_2$F)$_2$ | CH$_3$ | CH$_3$ | CH$_3$ | H |
| F | Cl | SCH$_2$COOC$_4$H$_9$ | CH$_3$ | CH$_3$ | CH$_3$ | H |
| F | Cl | SCH$_2$COO-cyclopentyl | CH$_3$ | CH$_3$ | CH$_3$ | H |
| F | Cl | SCH$_2$COOCH$_2$-(tetrahydrofuran-2-yl) | CH$_3$ | CH$_3$ | CH$_3$ | H |
| F | Cl | SCHCOOCH$_3$ \| CH$_3$ | CH$_3$ | CH$_3$ | CH$_3$ | H |
| H | Cl | SCH$_2$CH=CH$_2$ | CH$_3$ | CH$_3$ | C$_2$H$_5$ | H |
| H | Cl | SCH$_2$CH=CHCl | CH$_3$ | CH$_3$ | C$_2$H$_5$ | H |
| H | Cl | SCH$_2$C≡CH | CH$_3$ | CH$_3$ | C$_2$H$_5$ | H |
| H | Cl | SCHC≡CH \| CH$_3$ | CH$_3$ | CH$_3$ | C$_2$H$_5$ | H |
| H | Cl | SCF$_2$CHFCl | CH$_3$ | CH$_3$ | C$_2$H$_5$ | H |
| H | Cl | SCH(CH$_2$F)$_2$ | CH$_3$ | CH$_3$ | C$_2$H$_5$ | H |
| H | Cl | SCH$_2$CH$_2$CN | CH$_3$ | CH$_3$ | C$_2$H$_5$ | H |
| H | Cl | SCH$_2$CH$_2$COOC$_2$H$_5$ | CH$_3$ | CH$_3$ | C$_2$H$_5$ | H |
| H | Cl | SCH$_2$COOC$_4$H$_9$ | CH$_3$ | CH$_3$ | C$_2$H$_5$ | H |
| H | Cl | SCH$_2$COO-cyclopentyl | CH$_3$ | CH$_3$ | C$_2$H$_5$ | H |
| H | Cl | SCHCOOCH$_3$ \| CH$_3$ | CH$_3$ | CH$_3$ | C$_2$H$_5$ | H |
| F | Cl | SCH$_2$CH=CHCl | CH$_3$ | CH$_3$ | C$_2$H$_5$ | H |
| F | Cl | SCH$_2$C≡CH | CH$_3$ | CH$_3$ | C$_2$H$_5$ | H |
| F | Cl | SC(CH$_3$)$_2$C≡CH | CH$_3$ | CH$_3$ | C$_2$H$_5$ | H |
| F | Cl | SCH$_2$CH$_2$COOCH$_3$ | CH$_3$ | CH$_3$ | C$_2$H$_5$ | H |
| F | Cl | SCH$_2$COO-cyclopentyl | CH$_3$ | CH$_3$ | C$_2$H$_5$ | H |
| F | Cl | SCH(CH$_2$F)$_2$ | CH$_3$ | CH$_3$ | C$_2$H$_5$ | H |
| F | Cl | SCH$_2$CH$_2$COOCH$_3$ | CH$_3$ | CH$_3$ | C$_2$H$_5$ | H |
| F | Cl | SCHCOOCH$_3$ \| CH$_3$ | CH$_3$ | CH$_3$ | C$_2$H$_5$ | H |
| H | CN | OCH$_2$CH=CH$_2$ | CH$_3$ | CH$_3$ | C$_2$H$_5$ | H |

TABLE 1-continued

| | | | | | | |
|---|---|---|---|---|---|---|
| H | CN | OCHF$_2$ | CH$_3$ | CH$_3$ | C$_2$H$_5$ | H |
| H | CN | OCF$_2$CHFCl | CH$_3$ | CH$_3$ | C$_2$H$_5$ | H |
| H | CN | OCH$_2$C≡CH | CH$_3$ | CH$_3$ | C$_2$H$_5$ | H |
| H | CN | SCH$_2$C≡CH | CH$_3$ | CH$_3$ | C$_2$H$_5$ | H |
| H | CN | SCHC≡CH<br>\|<br>CH$_3$ | CH$_3$ | CH$_3$ | C$_2$H$_5$ | H |
| H | CN | SCH$_2$COOC$_3$H$_7$ | CH$_3$ | CH$_3$ | C$_2$H$_5$ | H |
| H | CN | SCH$_2$COO—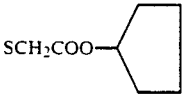 | CH$_3$ | CH$_3$ | C$_2$H$_5$ | H |
| H | CN | SCHCOOC$_2$H$_5$<br>\|<br>CH$_3$ | CH$_3$ | CH$_3$ | C$_2$H$_5$ | H |
| F | CN | OCH$_2$CH=CHCH$_3$ | CH$_3$ | CH$_3$ | C$_2$H$_5$ | H |
| F | CN | OCH$_2$C≡CH | CH$_3$ | CH$_3$ | C$_2$H$_5$ | H |
| F | CN | OCH$_2$COOC$_4$H$_9$ | CH$_3$ | CH$_3$ | C$_2$H$_5$ | H |
| F | CN | O(CH$_2$CH$_2$O)$_2$C$_2$H$_5$ | CH$_3$ | CH$_3$ | C$_2$H$_5$ | H |
| F | CN | SCH$_2$CH=CH$_2$ | CH$_3$ | CH$_3$ | C$_2$H$_5$ | H |
| F | CN | SCH$_2$CH=CHCl | CH$_3$ | CH$_3$ | C$_2$H$_5$ | H |
| F | CN | SCH$_2$CH$_2$CN | CH$_3$ | CH$_3$ | C$_2$H$_5$ | H |
| F | CN | SCH$_2$COOC$_2$H$_5$ | CH$_3$ | CH$_3$ | C$_2$H$_5$ | H |
| F | CN | SCH$_2$CH$_2$COOCH$_3$ | CH$_3$ | CH$_3$ | C$_2$H$_5$ | H |
| F | CN | SCHCOOCH$_3$<br>\|<br>CH$_3$ | CH$_3$ | CH$_3$ | C$_2$H$_5$ | H |
| H | Cl | SCH$_2$CH=CH$_2$ | CH$_3$ | CH$_3$ | C$_3$H$_7$ | H |
| H | Cl | SCH$_2$C≡CH | CH$_3$ | CH$_3$ | C$_3$H$_7$ | H |
| H | Cl | SCHC≡CH<br>\|<br>CH$_3$ | CH$_3$ | CH$_3$ | C$_3$H$_7$ | H |
| H | Cl | SCH$_2$COOC$_4$H$_9$ | CH$_3$ | CH$_3$ | C$_3$H$_7$ | H |
| H | Cl | SCH$_2$CH$_2$CN | CH$_3$ | CH$_3$ | C$_3$H$_7$ | H |
| H | Cl | SCH$_2$CH$_2$COOCH$_3$ | CH$_3$ | CH$_3$ | C$_3$H$_7$ | H |
| H | Cl | SCH(CH$_2$F)$_2$ | CH$_3$ | CH$_3$ | C$_3$H$_7$ | H |
| H | Cl | SCHCOOCH$_3$<br>\|<br>CH$_3$ | CH$_3$ | CH$_3$ | C$_3$H$_7$ | H |
| F | Cl | SCH$_2$CH=CH$_2$ | CH$_3$ | CH$_3$ | C$_3$H$_7$ | H |
| F | Cl | SCH$_2$CH=CHCl | CH$_3$ | CH$_3$ | C$_3$H$_7$ | H |
| F | Cl | SCHC≡CH<br>\|<br>CH$_3$ | CH$_3$ | CH$_3$ | C$_3$H$_7$ | H |
| F | Cl | SCH$_2$C=CH$_2$<br>\|<br>Cl | CH$_3$ | CH$_3$ | C$_3$H$_7$ | H |
| F | Cl | SCH$_2$CH$_2$CN | CH$_3$ | CH$_3$ | C$_3$H$_7$ | H |
| F | Cl | SCH(CH$_2$F)$_2$ | CH$_3$ | CH$_3$ | C$_3$H$_7$ | H |
| F | Cl | SCH$_2$COOC$_3$H$_7$ | CH$_3$ | CH$_3$ | C$_3$H$_7$ | H |
| F | Cl | SCH$_2$COO—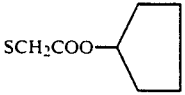 | CH$_3$ | CH$_3$ | C$_3$H$_7$ | H |
| F | Cl | SCHCOOCH$_3$<br>\|<br>CH$_3$ | CH$_3$ | CH$_3$ | C$_3$H$_7$ | H |
| H | CN | OCH$_2$CH=CH$_2$ | CH$_3$ | CH$_3$ | C$_3$H$_7$ | H |
| H | CN | OCH$_2$C≡CH | CH$_3$ | CH$_3$ | C$_3$H$_7$ | H |
| H | CN | OCHF$_2$ | CH$_3$ | CH$_3$ | C$_3$H$_7$ | H |
| H | CN | OCF$_2$CHF$_2$ | CH$_3$ | CH$_3$ | C$_3$H$_7$ | H |
| H | CN | OCH(CH$_2$F)$_2$ | CH$_3$ | CH$_3$ | C$_3$H$_7$ | H |

TABLE 1-continued

| | | | | | | |
|---|---|---|---|---|---|---|
| H | CN | OCH$_2$COOC$_4$H$_9$ | CH$_3$ | CH$_3$ | C$_3$H$_7$ | H |
| H | CN | OCH$_2$COOCH$_2$-(tetrahydrofuran-2-yl) | CH$_3$ | CH$_3$ | C$_3$H$_7$ | H |
| H | CN | SCH$_2$CH=CHCl | CH$_3$ | CH$_3$ | C$_3$H$_7$ | H |
| H | CN | SCH$_2$C≡CH | CH$_3$ | CH$_3$ | C$_3$H$_7$ | H |
| H | CN | SCHC≡CH (CH$_3$) | CH$_3$ | CH$_3$ | C$_3$H$_7$ | H |
| H | CN | SCH$_2$COOC$_2$H$_5$ | CH$_3$ | CH$_3$ | C$_3$H$_7$ | H |
| H | CN | SCHCOOCH$_3$ (CH$_3$) | CH$_3$ | CH$_3$ | C$_3$H$_7$ | H |
| F | CN | OCH$_2$CH=CH$_2$ | CH$_3$ | CH$_3$ | C$_3$H$_7$ | H |
| F | CN | OCH$_2$C≡CCH$_3$ | CH$_3$ | CH$_3$ | C$_3$H$_7$ | H |
| F | CN | OCH$_2$COOC$_2$H$_5$ | CH$_3$ | CH$_3$ | C$_3$H$_7$ | H |
| F | CN | SCH$_2$CH=CHCl | CH$_3$ | CH$_3$ | C$_3$H$_7$ | H |
| F | CN | SCH$_2$C≡CCH$_3$ | CH$_3$ | CH$_3$ | C$_3$H$_7$ | H |
| F | CN | SCH$_2$COOCH$_3$ | CH$_3$ | CH$_3$ | C$_3$H$_7$ | H |
| F | CN | SCH$_2$CH$_2$COOCH$_3$ | CH$_3$ | XH$_3$ | C$_3$H$_7$ | H |
| F | CN | SCH$_2$COO-(cyclopentyl) | CH$_3$ | CH$_3$ | C$_3$H$_7$ | H |
| F | CN | SCHCOOCH$_3$ (CH$_3$) | CH$_3$ | CH$_3$ | C$_3$H$_7$ | H |
| H | Cl | SCH$_2$CH=CH$_2$ | CH$_3$ | CH$_3$ | CH$_3$ | CH$_3$ |
| H | Cl | SCH$_2$CH=CHCl | CH$_3$ | CH$_3$ | CH$_3$ | CH$_3$ |
| H | Cl | SCH$_2$C≡CH | CH$_3$ | CH$_3$ | CH$_3$ | CH$_3$ |
| H | Cl | SCH$_2$C≡CCH$_3$ | CH$_3$ | CH$_3$ | CH$_3$ | CH$_3$ |
| H | Cl | SCHC≡CH (CH$_3$) | CH$_3$ | CH$_3$ | CH$_3$ | CH$_3$ |
| H | Cl | SCH$_2$CH$_2$CN | CH$_3$ | CH$_3$ | CH$_3$ | CH$_3$ |
| H | Cl | SCH$_2$COOC$_4$H$_9$ | CH$_3$ | CH$_3$ | CH$_3$ | CH$_3$ |
| H | Cl | SCHCOOC$_2$H$_5$ (CH$_3$) | CH$_3$ | CH$_3$ | CH$_3$ | CH$_3$ |
| F | Cl | SCH$_2$CH=CH$_2$ | CH$_3$ | CH$_3$ | CH$_3$ | CH$_3$ |
| F | Cl | SCH$_2$CH=CHCl | CH$_3$ | CH$_3$ | CH$_3$ | CH$_3$ |
| F | Cl | SCH$_2$C≡CH | CH$_3$ | CH$_3$ | CH$_3$ | CH$_3$ |
| F | Cl | SCH$_2$C≡CCH$_3$ | CH$_3$ | CH$_3$ | CH$_3$ | CH$_3$ |
| F | Cl | SCHC≡CH (CH$_3$) | CH$_3$ | CH$_3$ | CH$_3$ | CH$_3$ |
| F | Cl | SCH(CH$_2$F)$_2$ | CH$_3$ | CH$_3$ | CH$_3$ | CH$_3$ |
| F | Cl | SCH$_2$CH$_2$CN | CH$_3$ | CH$_3$ | CH$_3$ | CH$_3$ |
| F | Cl | SCH$_2$COOC$_3$H$_7$ | CH$_3$ | CH$_3$ | CH$_3$ | CH$_3$ |
| F | Cl | SCH$_2$COO-(cyclopentyl) | CH$_3$ | CH$_3$ | CH$_3$ | CH$_3$ |
| F | Cl | SCHCOOCH$_3$ (CH$_3$) | CH$_3$ | CH$_3$ | CH$_3$ | CH$_3$ |
| H | CN | OCH$_2$CH=CHCH$_3$ | CH$_3$ | CH$_3$ | CH$_3$ | CH$_3$ |
| H | CN | OCH$_2$CH=CHCl | CH$_3$ | CH$_3$ | CH$_3$ | CH$_3$ |
| H | CN | OCH$_2$C≡CH | CH$_3$ | CH$_3$ | CH$_3$ | CH$_3$ |
| H | CN | OCHF$_2$ | CH$_3$ | CH$_3$ | CH$_3$ | CH$_3$ |

TABLE 1-continued

| | | | | | | |
|---|---|---|---|---|---|---|
| H | CN | OCH$_2$COOC$_4$H$_9$ | CH$_3$ | CH$_3$ | CH$_3$ | CH$_3$ |
| H | CN | O(CH$_2$CH$_2$O)$_2$C$_2$H$_5$ | CH$_3$ | CH$_3$ | CH$_3$ | CH$_3$ |
| H | CN | SCH$_2$CH=CH$_2$ | CH$_3$ | CH$_3$ | CH$_3$ | CH$_3$ |
| H | CN | SCH$_2$C≡CH | CH$_3$ | CH$_3$ | CH$_3$ | CH$_3$ |
| H | CN | SCH(CH$_2$F)$_2$ | CH$_3$ | CH$_3$ | CH$_3$ | CH$_3$ |
| H | CN | SCH$_2$CH$_2$CN | CH$_3$ | CH$_3$ | CH$_3$ | CH$_3$ |
| H | CN | SCH$_2$COOC$_2$H$_5$ | CH$_3$ | CH$_3$ | CH$_3$ | CH$_3$ |
| H | CN | SCHCOOCH$_3$<br>\|<br>CH$_3$ | CH$_3$ | CH$_3$ | CH$_3$ | CH$_3$ |
| F | CN | OCH$_2$CH=CH$_2$ | CH$_3$ | CH$_3$ | CH$_3$ | CH$_3$ |
| F | CN | OCH$_2$C≡CH | CH$_3$ | CH$_3$ | CH$_3$ | CH$_3$ |
| F | CN | OCF$_2$CHFCl | CH$_3$ | CH$_3$ | CH$_3$ | CH$_3$ |
| F | CN | OCH$_2$COOC$_2$H$_5$ | CH$_3$ | CH$_3$ | CH$_3$ | CH$_3$ |
| F | CN | OCHCOOCH$_3$<br>\|<br>CH$_3$ | CH$_3$ | CH$_3$ | CH$_3$ | CH$_3$ |
| F | CN | O(CH$_2$CH$_2$O)$_2$CH$_3$ | CH$_3$ | CH$_3$ | CH$_3$ | CH$_3$ |
| F | CN | SCH$_2$CH=CH$_2$ | CH$_3$ | CH$_3$ | CH$_3$ | CH$_3$ |
| F | CN | SCH$_2$C≡CH | CH$_3$ | CH$_3$ | CH$_3$ | CH$_3$ |
| F | CN | SCH$_2$COOC$_3$H$_7$ | CH$_3$ | CH$_3$ | CH$_3$ | CH$_3$ |
| F | CN | SCHCOOC$_2$H$_5$<br>\|<br>CH$_3$ | CH$_3$ | CH$_3$ | CH$_3$ | CH$_3$ |
| H | Cl | SH | CH$_3$ | CH$_3$ | CH$_3$ | H |
| H | Cl | SH | CH$_3$ | CH$_3$ | C$_2$H$_5$ | H |
| H | Cl | SH | CH$_3$ | CH$_3$ | C$_3$H$_7$ | H |
| H | Cl | SH | CH$_3$ | CH$_3$ | —(CH$_2$)$_5$— | |
| H | Cl | SH | CH$_3$ | CH$_3$ | CH$_3$ | CH$_3$ |
| H | Cl | SH | CH$_3$ | CH$_3$ | H | H |
| F | Cl | SH | CH$_3$ | CH$_3$ | CH$_3$ | H |
| F | Cl | SH | CH$_3$ | CH$_3$ | CH$_3$ | CH$_3$ |
| F | Cl | SH | CH$_3$ | CH$_3$ | C$_2$H$_5$ | H |
| F | Cl | SH | CH$_3$ | CH$_3$ | C$_3$H$_7$ | H |
| F | Cl | SH | CH$_3$ | CH$_3$ | —(CH$_2$)$_5$— | |
| F | Cl | SH | CH$_3$ | CH$_3$ | H | H |
| H | CN | OH | CH$_3$ | CH$_3$ | H | CH$_3$ |
| H | CN | SH | CH$_3$ | CH$_3$ | CH$_3$ | H |
| H | CN | OH | CH$_3$ | CH$_3$ | C$_2$H$_5$ | H |
| H | CN | OH | CH$_3$ | CH$_3$ | C$_3$H$_7$ | H |
| H | CN | SH | CH$_3$ | CH$_3$ | C$_2$H$_5$ | H |
| H | CN | SH | CH$_3$ | CH$_3$ | C$_3$H$_7$ | H |
| H | CN | OH | CH$_3$ | CH$_3$ | —(CH$_2$)$_5$— | |
| H | CN | SH | CH$_3$ | CH$_3$ | —(CH$_2$)$_5$— | |
| H | CN | OH | CH$_3$ | CH$_3$ | H | H |
| H | CN | SH | CH$_3$ | CH$_3$ | H | H |
| F | CN | OH | CH$_3$ | CH$_3$ | CH$_3$ | H |
| F | CN | SH | CH$_3$ | CH$_3$ | CH$_3$ | H |
| F | CN | OH | CH$_3$ | CH$_3$ | C$_2$H$_5$ | H |
| F | CN | SH | CH$_3$ | CH$_3$ | C$_2$H$_5$ | H |
| F | CN | OH | CH$_3$ | CH$_3$ | C$_3$H$_7$ | H |
| F | CN | SH | CH$_3$ | CH$_3$ | C$_3$H$_7$ | H |
| F | CN | OH | CH$_3$ | CH$_3$ | —(CH$_2$)$_5$— | |
| F | CN | SH | CH$_3$ | CH$_3$ | —(CH$_2$)$_5$— | |
| F | CN | OH | CH$_3$ | CH$_3$ | H | H |
| F | CN | SH | CH$_3$ | CH$_3$ | H | H |
| H | CN | OH | —CH$_2$CHCH$_2$CH$_2$—<br>\|<br>CH$_3$ | | CH$_3$ | H |
| H | CN | SH | —CH$_2$CHCH$_2$CH$_2$—<br>\|<br>CH$_3$ | | CH$_3$ | H |
| H | CN | OH | —CH$_2$CHCH$_2$CH$_2$—<br>\|<br>CH$_3$ | | CH$_3$ | CH$_3$ |
| H | CN | SH | —CH$_2$CHCH$_2$CH$_2$—<br>\|<br>CH$_3$ | | CH$_3$ | CH$_3$ |

TABLE 1-continued

| | | | | | | |
|---|---|---|---|---|---|---|
| H | CN | OH | —CH$_2$CHCH$_2$CH$_2$—<br>      \|<br>     CH$_3$ | H | H | |
| H | CN | SH | —CH$_2$CHCH$_2$CH$_2$—<br>      \|<br>     CH$_3$ | H | H | |
| H | CN | OH | —CH$_2$CHCH$_2$CH$_2$—<br>      \|<br>     CH$_3$ | —(CH$_2$)$_5$— | | |
| H | CN | SH | —CH$_2$CHCH$_2$CH$_2$—<br>      \|<br>     CH$_3$ | —(CH$_2$)$_5$— | | |
| H | CN | OH | —(CH$_2$)$_4$— | CH$_3$ | H |
| H | CN | SH | —(CH$_2$)$_4$— | CH$_3$ | H |
| H | CN | OH | —(CH$_2$)$_4$— | CH$_3$ | CH$_3$ |
| H | CN | SH | —(CH$_2$)$_4$— | CH$_3$ | CH$_3$ |
| H | CN | OH | —(CH$_2$)$_4$— | —(CH$_2$)$_5$— | |
| H | CN | SH | —(CH$_2$)$_4$— | —(CH$_2$)$_5$— | |
| H | CN | OH | —(CH$_2$)$_4$— | H | H |
| H | CN | SH | —(CH$_2$)$_4$— | H | H |
| F | CN | OH | —(CH$_2$)$_4$— | CH$_3$ | H |
| F | CN | SH | —(CH$_2$)$_4$— | CH$_3$ | H |
| F | CN | OH | —(CH$_2$)$_4$— | CH$_3$ | CH$_3$ |
| F | CN | SH | —(CH$_2$)$_4$— | CH$_3$ | CH$_3$ |
| F | CN | OH | —(CH$_2$)$_4$— | —(CH$_2$)$_5$— | |
| F | CN | SH | —(CH$_2$)$_4$— | —(CH$_2$)$_5$— | |
| F | CN | OH | —(CH$_2$)$_4$— | H | H |
| F | CN | SH | —(CH$_2$)$_4$— | H | H |
| F | CN | OH | —CH$_2$CHCH$_2$CH$_2$—<br>      \|<br>     CH$_3$ | CH$_3$ | H |
| F | CN | SH | —CH$_2$CHCH$_2$CH$_2$—<br>      \|<br>     CH$_3$ | CH$_3$ | H |
| F | CN | OH | —CH$_2$CHCH$_2$CH$_2$—<br>      \|<br>     CH$_3$ | CH$_3$ | CH$_3$ |
| F | CN | SH | —CH$_2$CHCH$_2$CH$_2$—<br>      \|<br>     CH$_3$ | CH$_3$ | CH$_3$ |
| F | CN | OH | —CH$_2$CHCH$_2$CH$_2$—<br>      \|<br>     CH$_3$ | —(CH$_2$)$_5$— | |
| F | CN | SH | —CH$_2$CHCH$_2$CH$_2$—<br>      \|<br>     CH$_3$ | —(CH$_2$)$_5$— | |
| F | CN | OH | —CH$_2$CHCH$_2$CH$_2$—<br>      \|<br>     CH$_3$ | H | H |
| F | CN | SH | —CH$_2$CHCH$_2$CH$_2$—<br>      \|<br>     CH$_3$ | H | H |
| H | Cl | SH | —(CH$_2$)$_4$— | CH$_3$ | H |
| H | Cl | SH | —(CH$_2$)$_4$— | C$_2$H$_5$ | H |
| H | Cl | SH | —(CH$_2$)$_4$— | C$_3$H$_7$ | H |
| H | Cl | SH | —(CH$_2$)$_4$— | CH$_3$ | CH$_3$ |
| H | Cl | SH | —(CH$_2$)$_4$— | —(CH$_2$)$_5$— | |
| H | Cl | SH | —(CH$_2$)$_4$— | H | H |
| H | Cl | SH | —CH$_2$CHCH$_2$CH$_2$—<br>      \|<br>     CH$_3$ | CH$_3$ | H |
| H | Cl | SH | —CH$_2$CHCH$_2$CH$_2$—<br>      \|<br>     CH$_3$ | C$_2$H$_5$ | H |

TABLE 1-continued

| | | | | | |
|---|---|---|---|---|---|
| H | Cl | SH | —CH$_2$CHCH$_2$CH$_2$—<br>    \|<br>    CH$_3$ | C$_3$H$_7$ | H |
| H | Cl | SH | —CH$_2$CHCH$_2$CH$_2$—<br>    \|<br>    CH$_3$ | CH$_3$ | CH$_3$ |
| H | Cl | SH | —CH$_2$CHCH$_2$CH$_2$—<br>    \|<br>    CH$_3$ | —(CH$_2$)$_5$— | |
| H | Cl | SH | —CH$_2$CHCH$_2$CH$_2$—<br>    \|<br>    CH$_3$ | H | H |
| F | Cl | SH | —(CH$_2$)$_4$— | CH$_3$ | H |
| F | Cl | SH | —(CH$_2$)$_4$— | C$_2$H$_5$ | H |
| F | Cl | SH | —(CH$_2$)$_4$— | C$_3$H$_7$ | H |
| F | Cl | SH | —(CH$_2$)$_4$— | CH$_3$ | CH$_3$ |
| F | Cl | SH | —(CH$_2$)$_4$— | —(CH$_2$)$_5$— | |
| F | Cl | SH | —(CH$_2$)$_4$— | H | H |
| F | Cl | SH | —CH$_2$CHCH$_2$CH$_2$—<br>    \|<br>    CH$_3$ | CH$_3$ | H |
| F | Cl | SH | —CH$_2$CHCH$_2$CH$_2$—<br>    \|<br>    CH$_3$ | C$_2$H$_5$ | H |
| F | Cl | SH | —CH$_2$CHCH$_2$CH$_2$—<br>    \|<br>    CH$_3$ | C$_3$H$_7$ | H |
| F | Cl | SH | —CH$_2$CHCH$_2$CH$_2$—<br>    \|<br>    CH$_3$ | CH$_3$ | CH$_3$ |
| F | Cl | SH | —CH$_2$CHCH$_2$CH$_2$—<br>    \|<br>    CH$_3$ | —(CH$_2$)$_5$— | |
| F | Cl | SH | —CH$_2$CHCH$_2$CH$_2$—<br>    \|<br>    CH$_3$ | H | H |

If, for example, 2-acetyl-cyclohexene-1-carboxylic acid and 2-fluoro-4-cyano-5-allyloxy-aniline are used as starting substances for process (a) according to the invention, the course of the reaction can be represented by the following equation:

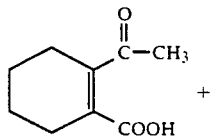
+
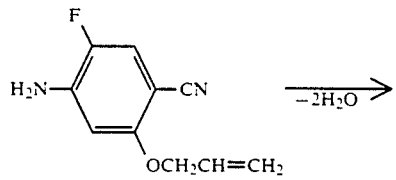

If, for example, N-(2-fluoro-4-methyl-5-propargyloxy-phenyl)-3,4,5,6-tetrahydro-phthalimide and propylmagnesium bromide are used as starting substances for process (b) according to the invention, the course of the reaction can be represented by the following equation:

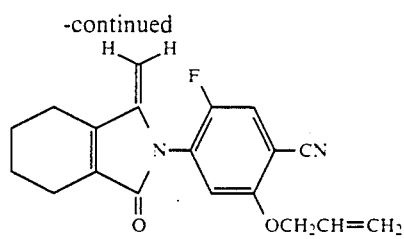

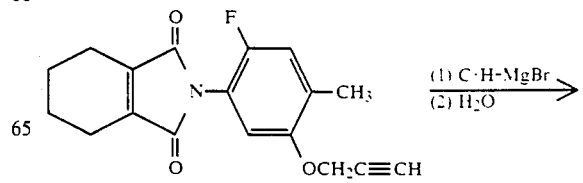

-continued

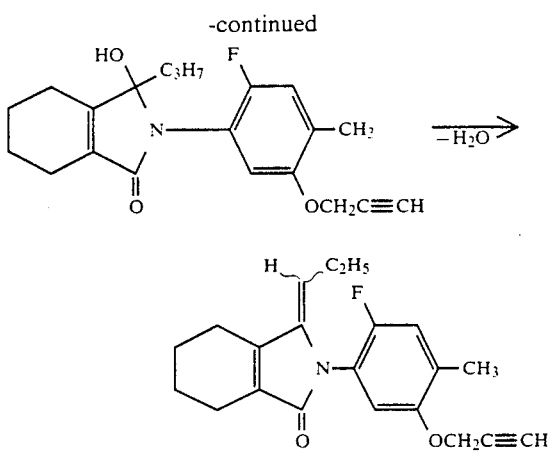

If, for example, 2-(2-fluoro-4-cyano-5-hydroxy-phenyl)-3-methylene-4,5, 6,7-tetrahydro-2H-isoindol-1-one and ethyl bromoacetate are used as starting substances for process (c) according to the invention, the course of the reaction can be represented by the following equation:

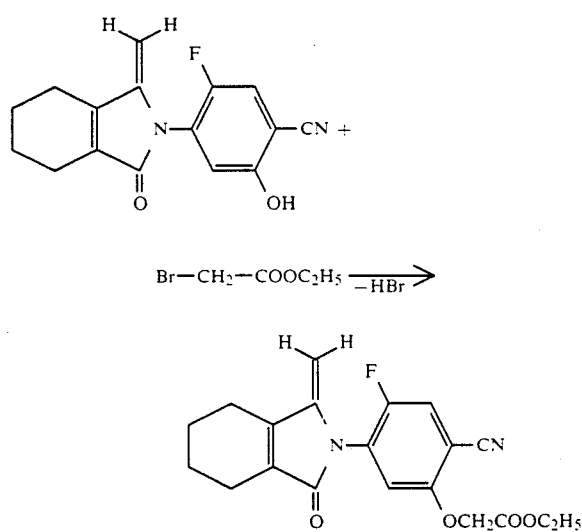

If, for example, 1-(2,5-difluoro-4-cyano-phenyl)5-iso-propylidene-3,4-dimethyl-1H-pyrrol-2-one and allyl alcohol are used as starting substances for process (d) according to the invention, the course of the reaction can be represented by the following equation:

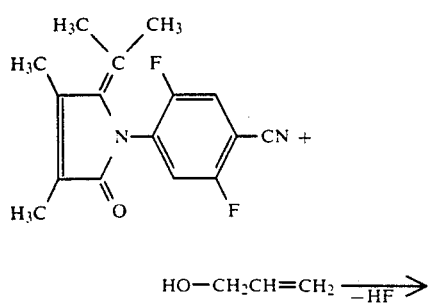

-continued

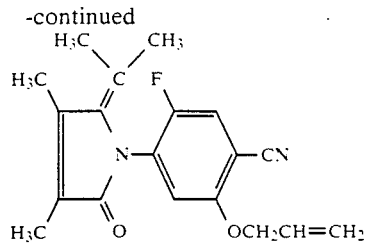

Formula (II) provides a general definition of the keto-carboxylic acids to be used as starting substances for the preparation of the compounds of the formula (I) in process (a) according to the invention.

In formula (II), $R^4$, $R^5$, $R^6$ and $R^7$ preferably or in particular have those meanings which have already been mentioned above as preferred or as particularly preferred for $R^4$, $R^5$, $R^6$ and $R^7$ in connection with the description of the compounds of the formula (I) according to the invention.

The starting substances of the formula (II) are known and/or can be prepared by processes which are known per se (compare Helv.Chim.Acta 50 (1967), 798–807).

Formula (III) provides a general definition of the arylamines also to be used as starting substances in process (a) according to the invention.

In formula (III), $R^1$, $R^2$ and $R^3$ preferably or in particular have those meanings which have already been mentioned above as preferred or as -particularly preferred for $R^1$, $R^2$ and $R^3$ in connection with the description of the compounds of the formula (I) according to the invention.

The starting substances of the formula (III) are known and/or can be prepared by processes which are known per se (compare EP-A 69,855, EP-A 70,389, EP-A 75,267 and EP-A 290,902).

Formula (IV) provides a general definition of the N-aryl-imides to be used as starting substances for the preparation of the compounds of the formula (I) in process (b) according to the invention.

In formula (IV), $R^1$, $R^2$, $R^3$, $R^4$ and $R^5$ preferably or in particular have those meanings which have already been mentioned above as preferred or as particularly preferred for $R^1$, $R^2$, $R^3$, $R^4$ and $R^5$ in connection with the description of the compounds of the formula (I) according to the invention.

The starting substances of the formula (IV) are known and/or can be prepared by processes which are known per se (compare EP-A 61,741, EP-A 83,055, EP-A 126,419, EP-A 211,805 and EP-A 303,573).

Formula (V) provides a general definition of the organometallic compounds furthermore to be used as starting substances in process (b) according to the invention.

In formula (V), $R^6$ and $R^7$ preferably or in particular have those meanings which have already been mentioned above as preferred or as particularly preferred for $R^6$ and $R^7$ in connection with the description of the compounds of the formula (I) according to the invention and M preferably represents lithium or the grouping MgX, wherein X represents chlorine, bromine or iodine.

The starting substances of the formula (V) are known synthesis chemicals.

The hydroxy compounds of the formula (VI) obtained as intermediate products in process (b) according to the invention are new and the present invention relates to these compounds. The compounds of the formula (VI) also have a herbicidal action to a certain degree.

Formula (I) provides a general definition of the compounds to be used as starting substances in process (c) according to the invention, with the proviso that $R^3$ represents hydroxyl or mercapto.

In this case, $R^1$, $R^2$, $R^4$, $R^5$, $R^6$ and $R^7$ preferably or in particular have those meanings which have been mentioned above as preferred or as particularly preferred for $R^1$, $R^2$, $R^4$, $R^5$, $R^6$ and $R^7$ in the context of the description of the compounds of the formula (I) according to the invention.

The starting substances of the formula (I) described above for process (c) are new compounds according to the invention; they can be prepared by processes (a) and (b) according to the invention.

Formula (VII) provides a general definition of the alkylating agents furthermore to be used as starting substances in process (c).

Preferably, in formula (VII), $R^8$ represents optionally substituted straight-chain or branched alkyl having up to 8 carbon atoms, possible substituents being: fluorine, chlorine, bromine, cyano, carboxyl, $C_1$-$C_4$-alkoxy, $C_1$-$C_4$-alkoxy-$C_1$-$C_4$-alkoxy, $C_1$-$C_4$-alkylthio, $C_1$-$C_4$-alkyl-carbonyl, $C_1$-$C_4$-alkoxy-carbonyl, $C_3$-$C_6$-cycloalkoxy-carbonyl, $C_3$-$C_6$-cycloalkyl-$C_1$-$C_2$-alkoxy,carbonyl, $C_5$-$C_6$-cycloalkenyloxy-carbonyl, $C_5$-$C_6$-cycloalkenyl-$C_1$-$C_2$-alkoxy-carbonyl and tetrahydrofurylmethoxycarbonyl; $R^8$ furthermore preferably represents in each case optionally substituted and optionally branched alkenyl, alkinyl or cycloalkyl having in each case up to 8 carbon atoms, possible substituents being: fluorine, chlorine, bromine, cyano, carboxyl and $C_1$-$C_4$-akloxy-carbonyl, and furthermore, preferably, X represents chlorine, bromine, iodine, methylsulfonyloxy, phenylsulfonyloxy, tolylsulfonyloxy, methoxysulfonyloxy or ethoxysulfonyloxy.

In formula (VII), in particular, $R^8$ represents in each case optionally substituted methyl, ethyl, propyl, isopropyl, butyl, isobutyl, sec-butyl, tert-butyl, pentyl, isopentyl, secpentyl, tert-pentyl, hexyl or isohexyl, possible substituents being, inparticular: fluorine, chlorine, cyano, carboxyl, methoxy, ethoxy, propoxy, isopropoxy, methoxyethoxy, ethoxyethoxy, methylthio, ethylthio, propylthio, isopropylthio, methylcarbonyl, ethylcarbonyl, propylcarbonyl, isopropylcarbonyl, butylcarbonyl, isobutylcarbonyl, sec-butylcarbonyl, tert-butylcarbonyl, methoxycarbonyl, ethoxycarbonyl, propoxycarbonyl, isopropoxycarbonyl, butoxycarbonyl, isobutoxycarbonyl, sec-butoxycarbonyl, tert-butoxy-carbonyl, cyclopropyloxycarbonyl, cyclopentyloxy-carbonyl, cyclohexyloxycarbonyl, cyclopentenyloxy-carbonyl, cyclohexenyloxycarbonyl, cyclopropylmethoxycarbonyl, cyclopentylmethoxycarbonyl, cyclohexylmethoxycarbonyl, cyclopentenylmethoxycarbonyl, cyclohexenylmethoxycarbonyl and tetrahydrofurylmethoxycarbonyl; or furthermore $R^8$ in particular represents allyl, 1-methyl-, 2-methylor 3-methyl-allyl, propargyl, 1-methyl-, 3-methylor 1,1-dimethyl-propargyl, cyclopropyl, cyclopentyl or cyclohexyl, which are in each case optionally substituted by fluorine and/or chlorine, and X represents chlorine, bromine or iodine.

The starting substances of the formula (VII) are known organic synthesis chemicals.

Formula (I) provides a general definition of the compounds to be used as starting substances in process (d) according to the invention, with the proviso that $R^3$ represents halogen.

In this case, $R^1$, $R^2$, $R^4$, $R^5$, $R^6$ and $R^7$ preferably or in particular have those meanings which have been mentioned above as preferred or as particularly preferred for $R^1$, $R^2$, $R^4$, $R^5$, $R^6$ and $R^7$ in the context of the description of the compounds of the formula (I) according to the invention, and $R^3$ preferably represents fluorine, chlorine or bromine.

The starting substances of the formula (I) described above for process (d) are new compounds according to the invention; they can be prepared by processes (a) or (b) according to the invention.

Formula (VIII) provides a general definition of the compounds furthermore to be used as starting substances in process (d).

In formula (VIII), $R^9$ preferably or in particular has that meaning which has been mentioned above as preferred or as particularly preferred for $R^3$ in connection with the description of the compounds of the formula (I) according to the invention, but excluding fluorine, chlorine and bromine. Preferred metal salts of this are the corresponding lithium, sodium and potassium salts.

The starting substances of the formula (VIII) are known organic synthesis chemicals.

If appropriate, process (a) according to the invention for the preparation of the new compounds of the formula (I) is carried out using diluents. Possible diluents here are virtually all the inert organic solvents. These include, preferably, aliphatic and aromatic, optionally halogenated hydrocarbons, such as benzine, benzene, toluene, xylene and chlorobenzene. However, in many cases process (a) can also be carried out without using a diluent.

Process (a) according to the invention is preferably carried out in the presence of an acid catalyst. Possible acid catalysts are, above all, proton acids, such as hydrochloric acid, sulphuric acid, sodium hydrogen sulphate or potassium hydrogen sulphate, methanesulphonic acid, benzenesulphonic acid and p-toluenesulphonic acid.

The reaction temperatures can be varied within a fairly large range in process (a) according to the invention. The reaction is in general carried out at temperatures between 20° C. and 200° C., preferably at temperatures between 60° C. and 150° C.

Process (a) according to the invention is in general carried out under normal pressure. However, it is also possible for the reaction to be carried out under increased or reduced pressure.

For carrying out process (a) according to the invention, in general between 0.6 and 1.4 mols, preferably between 0.8 and 1.2 mols, of arylamine of the formula (III) are employed per mol of ketocarboxylic acid of the formula (II).

The starting substances of the formulae (II) and (III) are in general mixed with the acid catalyst and if appropriate the diluent at room temperature, and the mixture is then stirred, preferably at elevated temperature, until the reaction has ended. Working up can be carried out by customary methods (compare the preparation examples).

Process (b) according to the invention for the preparation of the new compounds of the formula (I) is preferably carried out using diluents. Possible diluents are virtually all the inert organic solvents. These include, preferably, aliphatic and aromatic hydrocarbons, such as pentane, hexane, heptane, cyclohexane, benzene and toluene, and ethers, such as diethyl ether, dipropyl ether, diisopropyl ether, dibutyl ether, diisobutyl ether, tetrahydrofuran, dioxane and 1,2-dimethoxyethane.

The reaction temperatures can be varied within a fairly large range in the first stage of process (b) according to the invention. The reaction is in general carried out at temperatures between −50° C. and +100° C., preferably at temperatures between 0° C. and +50° C.

Process (b) according to the invention is in general carried out under normal pressure. However, it is also possible for the process to be carried out under increased or reduced pressure.

For carrying out process (b) according to the invention, in general between 1 and 3 mols, preferably between 1.1 and 2.5 mols, of organometallic compound of the formula (V) are employed per mol of N-aryl-imide of the formula (IV).

The starting substances of the formulae (IV) and (V) are in general mixed with a solvent at room temperature or while cooling, the mixture is stirred until the reaction has ended, an aqueous acid, such as, for example, dilute hydrochloric acid, sulphuric acid or acetic acid, is then added and the mixture is worked up by customary methods for isolation of the compounds of the formula (VI) (compare the preparation examples).

The dehydration of these intermediates to give the corresponding compounds of the formula (I) is then carried out in a second stage by customary methods. Diluents and acid catalysts as described above for process (a) are preferably employed here. The reaction components are in general reacted analogously to process (a) and the working up is carried out by customary methods (compare the preparation examples).

Process (c) according to the invention for the preparation of the new compounds of the formula (I) is preferably carried out using diluents. Possible diluents here are, in addition to water, virtually all the inert organic solvents. These include, preferably, aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether, dibutyl ether, glycol dimethyl ether, diglycol dimethyl ether, tetrahydrofuran and dioxane, ketones, such as acetone, methyl ethyl ketone, methyl isopropyl ketone and methyl isobutyl ketone, esters, such as methyl and ethyl acetate, nitriles, such as, for example, acetonitrile and propionitrile, amides, such as, for example, dimethylformamide, dimethylacetamide and N-methyl-pyrrolidone, and dimethyl sulphoxide, tetramethylene sulphone and hexamethylphosphoric triamide.

Acid acceptors which can be used in process (c) according to the invention are all the acid-binding agents which can customarily be employed for such reactions. Preferred possible acid-binding agents are alkali metal hydroxides, such as, for example, sodium hydroxide and potassium hydroxide, alkaline earth metal hydroxides, such as, for example, calcium hydroxide, alkali metal carbonates, hydrides and alcoholates, such as sodium carbonate, potassium carbonate, sodium hydride, potassium hydride, sodium tert.-butylate and potassium tert.-butylate, and furthermore aliphatic, aromatic or heterocyclic amines, for example triethylamine, trimethylamine, dimethylaniline, dimethylbenzylamine, pyridine, 1,5-diazabicyclo-[4,3,0]-non-5-ene 1,8-diazabicyclo [5,4,0]-undec-7-ene (DBU) and 1,4-diazabicyclo-[2,2,2]octane (DABCO).

The reaction temperatures can be varied within a more substantial range in process (c) according to the invention. The reaction is in general carried out at temperatures between −20° C. and +100° C., preferably at temperatures between 0° C. and +80° C.

Process (c) according to the invention is in general carried out under normal pressure. However, it is also possible for the process to be carried out under increased or reduced pressure.

For carrying out process (c) according to the invention, the particular starting substances required are in general employed in approximately equimolar amounts. However, it is also possible for one of the two particular components employed to be used in a larger excess. The reactions are in general carried out in a suitable diluent in the presence of an acid acceptor and the reaction mixture is stirred at the particular required temperature for several hours. Working up in process (c) according to the invention is in each case carried out by customary methods.

If appropriate, process (d) according to the invention for the preparation of the new compounds of the formula (I) is carried out in the presence of a diluent. The same solvents which are mentioned above for process (c) according to the invention are preferably suitable here.

If appropriate, process (d) according to the invention is carried out in the presence of an acid acceptor. The same acid-binding agents as are mentioned above for process (c) according to the invention are preferably suitable here.

The reaction temperatures can be varied within a substantial range in process (d) according to the invention. The reaction is in general carried out at temperatures between 0° C. and 150° C., preferably at temperatures between 10° C. and 100° C.

Process (d) according to the invention is in general carried out under normal pressure. However, it is also possible for the process to be carried out under increased or reduced pressure.

For carrying out process (d) according to the invention, the particular starting substances required are in general employed in approximately equimolar amounts. However, it is also possible for one of the two particular components employed to be used in a larger excess. The reactions are in general carried out in a suitable diluent in the presence of an acid acceptor, and the reaction mixture is stirred at the particular temperature required for several hours. Working up in process (d) according to the invention is in each case carried out by customary methods.

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the compounds according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total control of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The compounds of the formula (I) according to the invention are suitable for selectively combating monocotyledon and dicotyledon weeds in monocotyledon and dicotyledon crops both by the pre-emergence and by the postemergence method.

The active compounds according to the invention engage in the metabolism of the plants and can therefore be employed as growth regulators.

Experience to date of the mode of action of plant growth regulators has shown that an active compound can also exert several different actions on plants. The actions of the compounds depend essentially on the point in time at which they are used, relative to the stage of development of the plant, and on the amounts of active compound applied to the plants or their environment and on the way in which the compounds are applied. In every case, growth regulators are intended to influence the crop plants in the particular manner desired.

The amount of leaves on plants can be controlled, under the influence of growth regulators, so that defoliation of the plants at a desired point in time is achieved. Such defoliation is of great importance in the mechanical harvesting of cotton, but is also of interest for facilitating harvesting in other crops, such as, for example, in viniculture. Defoliation of the plants can also be carried out to lower the transpiration of plants before they are transplanted.

The active compounds can be converted into the customary formulations, such as solutions, emulsions, wettable powders, suspensions, powders, dusting agents, pastes, soluble powders, granules, suspension-/emulsion concentrates, natural and synthetic materials impregnated with active compound and very fine capsules in polymeric substances.

These formulations are produced in a known manner, for example by mixing the active compounds with extenders, that is, liquid solvents, and/or solid carriers, optionally with the use of surface-active agents, that is, emulsifying agents and/or dispersing agents, and/or foam-foaming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids can be used in the formulations. Further additives may be mineral and vegetable oils.

It is possible to use colorants such as inorganic pigments, for example iron oxide, titanium oxide and Prussian blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention, as such or in the form of their formulations, can also be used for combating weeds as mixtures with known herbicides, finished formulations or tank mixes being possible.

Suitable herbicides for the mixtures are known herbicides, such as, for example, 1-amino-6-ethylthio-3(2,2-dimethylpropyl)-1,3,5-triazine-2,4(1H,3H)-dione (AMETHYDIONE) or N-(2-benzothiazolyl)-N,N,-dimethylurea (METABENZTHIAZURON) for combating weeds in cereals; 4-amino-3-methyl-6-phenyl-1,2,4-triazin-5(4H)-one (META-MITRON) for combating weeds in sugar beets, and 4-amino-6-4-amino-6(1,1-dimethylethyl)-3-methylthio-1,2,4-triazin5(4H)-one (METRIBUZIN) for combating weeds in soy beans; furthermore also 2,4-dichlorophenoxyacetic acid (2,4-D); 4-(2,4-dichlorophenoxy)-butyric acid (2,4-DB); 2,4dichlorophenoxypropionic acid (2,4-DP); 5-(2-chloro-4-trifluoromethyl-phenoxy)-2-nitrobenzoic acid (ACIFLUORFEN); chloroacetic acid N-(methoxymethyl)-2,6-diethylanilide (ALACHLOR); methyl 6,6-dimethyl-2,4-dioxo-3-[1-(2-propenyloxyamino)-butylidene]-cyclohexanecarboxylate (ALLOXYDIM); 2-chloro-4-ethylamino-6-isopropylamino1,3,5-triazine (ATRAZIN); 3-isopropyl-2,1,3-benzothia-diazin-4-one 2,2-dioxide (BENTAZONE); methyl 5-(2,4-dichloro-phenoxy)-2-nitrobenzoate (BIFENOX); 3,5-dibromo4-hydroxy-benzonitrile (BROMOXYNIL); N-(butoxymethyl)-2-chloro-N-(2,6-diethylphenyl)-acetamide (BUTACHLOR);ethyl 2-{[(4-chloro-6-methoxy-2-pyrimidinyl)-aminocarbonyl]aminosulphonyl}-benzoate (CHLORIMURON); 2-chloro-N-{[(4-methoxy-6-methyl-1,3,5-triazin-2-yl)-amino]-carbonyl)benzenesulphonamide (CHLORSULFURON); N,N-dimethyl-N'-(3-chloro-4-methylphenyl)-urea(CHLORTOLURON); exo-1-methyl4-(1-methylethyl)-2-(2-methylphenyl-methoxy)-7-oxabi-cyclo-(2,2,1)-heptane (CINMETHYLIN); 3,6-dichloro-2pyridinecarboxylic acid (CLOPYRALID); 2-chloro-4-ethylamino-6-(3-cyano-propylamino)-1,3,5-triazine (CYANAZIN); 2-[4-(2,4-dichlorophenoxy)-phenoxy]-propionic acid and the methyl or ethyl ester thereof (DICLOFOP); 2-[(2-chlorophenyl)-methyl]-4,4-dimethylisoxazolidin-3-one (DIMETHAZONE); S-ethyl N,N-di-n-propyl-thiocarbamate (EPTAME); 4-amino-6-t-butyl-3-ethylthio-1,2,4-triazin-5(4H)-one (ETHIOZIN); 2-{4-[(6-chloro-2-benzoxazolyl)-oxy]-phenoxy}-propanoic acid and the methyl or ethyl ester thereof (FENOXAPROP); 2-[4-(5-trifluoromethyl-2-pyridyloxy)-phenoxy]-propanoic acid or the butyl ester thereof (FLUAZIFOP); [(4-amino-3,5-dichloro-6-fluoro-2-pyridinyl)-oxy]-acetic acid or the 1-methylheptyl ester thereof (FLUROX-YPYR); 5-(2-chloro-4-trifluoromethyl-phenoxy)-N-methylsulphonyl-2-nitrobenzamide (FOMESAFEN); 2-{4-[(3-chloro-5-(trifluoromethyl)-2-pyridinyl)-oxy]-phenoxy}-propanoic acid or the ethyl ester thereof (HALOXYFOP); 2-[4,5-dihydro-4-methyl-4-isopropyl-5-oxo-(1H)-imidazol-2-yl]-5-ethyl-pyridine-3-carboxylic acid (IMAZETHAPYR); 3,5-diiodo-4-hydroxybenzonitrile (IOXY-NIL); N,N-dimethyl-N'-(4-isopropylphenyl)-urea(ISOPROTURON); 2-ethoxy-1-methyl-2-oxo-ethyl 5-[2-chloro-4-(trifluoromethyl)-phenoxy]-2-nitrobenzoate (LACTOFEN); (2-methyl-4-chlorophenoxy)-acetic acid (MCPA); (4-chloro-2-methyl-phenoxy)-propionic acid (MCPP); N-methyl-2-(1,3-benzothiazol-2-yloxy)-acetanilide (MEFENACET); 2-chloro-N-(2,6-dimethylphenyl)-N-[(1H)-pyrazol-1-yl-methyl]acetamide (METAZACHLOR); 2-ethyl-6-methyl-N-(1-methyl-2-methoxyethyl)-chloroacetanilide (METOLACHLOR); 2-([[((4-methoxy-6-methyl-1,3,5-triazin-2-yl)-amino)-carbonyl]amino]-sulphonyl}-benzoic acid or the methyl ester thereof(METSULFURON);4-(di-n-propylamino)-3,5-dinitrobenzenesulphonamide (ORYZALIN); 2-chloro-4-trifluoromethylphenyl 3-ethoxy-4-nitro-phenyl ether (OXYFLUORFEN); N-(1-ethylpropyl)-3,4-dimethyl-2,6-dinitroaniline (PENDIMETHALIN); O-(6-chloro-3-phenyl-pyridazin-4-yl) S-octyl thiocarbonate (PYRI-DATE); ethyl 2-[4-(6-chloro-quinoxa-lin-2-yl-oxy)-phenoxy]-propionate (QUIZALOFOPETHYL); 2-[1-(ethoxamino)-butylidene]-5-(2-ethylthiopropyl)-1,3cy-clohexadione (SETHOXYDIM); 2-chloro-4,6-bis-(ethyl-amino)-1,3,5-triazine (SIMAZIN); 2,4-bis-[N-ethylamino]6-methylthio-1,3,5-triazine (SIMETRYNE); 4-ethylamino-2-t-butylamino-6-methylthio-s-triazine (TERBUTRYNE); methyl 3-[[[[(4-methoxy-6-methyl-1,3, 5-triazin-2-yl)-amino]carbonyl]-amino]-sulphonyl]-thiophene-2-carboxylate (THIAMETURON); S-[(4-chlorophenyl)-methyl]N,N-diethylthiocarbamate (THIOBENCARB); S-(2,3,3-trichloroallyl) N,N-diisopropyl-thiolcarbamate (TRIALLATE); and 2,6-dinitro-4-trifluoromethyl-N,N-dipropylaniline (TRIFLU-RALIN). Some mixtures surprisingly also exhibit a synergistic effect.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The amount of active compound used can vary within a fairly large range. It depends essentially on the nature of the desired effect. In general, the amounts used are between 0.001 and 5 kg of active compound per hectare of soil surface, preferably between 0.005 and 3 kg per ha.

The preparation and the use of the active compounds according to the invention can be seen from the following examples.

PREPARATION EXAMPLES

EXAMPLE 1

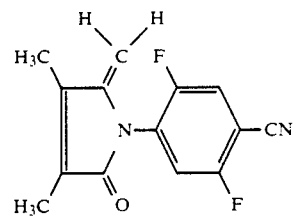

(Process (a))

A mixture of 20.0 g (0.141 mol) of 2,3-dimethyl4-oxo-2-pentenoic acid, 21.7 g (0.141 mol) of 2,5-di-fluoro-4-cyanoaniline and 4.0 g (0.02 mol) of p-toluenesulphonic acid is stirred at 110° C. for 12 hours, the water liberated being removed via a water separator. The mixture is then cooled and shaken with methylene chloride and 2N hydrochloric acid and the organic phase is separated off, washed with saturated sodium bicarbonate solution and concentrated. The residue is purified by chromatography (silica gel/diethyl ether).

10.7 g (29% of theory) of 1-(2,5-difluoro-4-cyano-phenyl)-3, 4-dimethyl-5-methylene-pyrrol-(1H)2-one of melting point 117° C. is obtained.

EXAMPLE 2

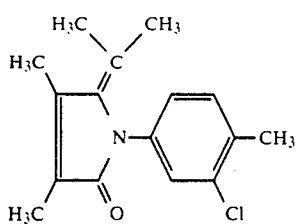

(Process (b))

Precursor: Example VI-1

A solution of 22.1 g (0.15 mol) of isopropylmagnesium bromide in 150 ml of diethyl ether is added dropwise to a solution of 25 g (0.10 mol) of N-(3-chloro4-methyl-phenyl)-dimethylmaleimide in 100 ml of tetrahydrofuran, while stirring, and the mixture is stirred at 20° C. for 6 hours. It is then acidified with 2N hydrochloric acid and the organic phase is separated off, washed with saturated sodium bicarbonate solution and dried with sodium sulphate. After filtration, the filtrate is concentrated, the residue is taken up in hexane and the undissolved starting substance is removed by filtration. The solvent is carefully distilled off from the filtrate under a waterpump vacuum.

20.9 g (71% of theory) of 1-(3-chloro-4-methyl-phenyl)-3, 4-dimethyl-5-hydroxy-5-isopropyl-pyrrol-(1H)2one are obtained as an amorphous residue.

$^1$H-NMR (CDCl$_3$, δ, ppm): 0.521 (CH$_3$), 0.544 (CH$_3$), 0.938 (CH$_3$), 0.962 (CH$_3$), 2.09 (CH$_3$).

Conversion into the compound according to Example 2:

14.3 g (48.7 mmol) of 1-(3-chloro-4-methyl-phenyl)-3, 4-dimethyl-5-hydroxy-5-isopropyl-pyrrol-(1H)2one are heated at the boiling point together with 2.0 g (10 mmol) of p-toluenesulphonic acid and 100 ml of toluene and the water liberated is removed using a water separator. After 6 hours, the mixture is cooled, washed with saturated sodium bicarbonate solution, dried with sodium sulphate and filtered. The filtrate is concentrated and the residue is purified by chromatography (silica gel/diisopropyl ether).

8.0 g (60% of theory) of 1-(3-chloro-4-methyl-phenyl)-3, 4-dimethyl-5-isopropylidene-pyrrol-(1H)2-one are obtained as an amorphous product.

$^1$H-NMR (CDCl$_3$,α, ppm): 2.086 (CH$_3$).

EXAMPLE 3

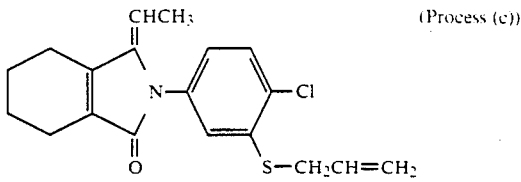

(Process (c))

3.0 g (0.025 mol) of allyl bromide are added dropwise to a mixture of 7.5 g (0.025 mol) of 2-(4-chloro-3-mercapto-phenyl)-3-ethylidene-4, 5,6,7-tetra-hydro-2H-isoindol-1-one, 1.4 g (0.025 mol) of potassium hydroxide, 10 ml of water and 50 ml of dimethyl sulphoxide, while stirring, and the mixture is stirred at 50° C. for a further 2 hours.

After cooling, the mixture is diluted with 300 ml of water and shaken with 300 ml of ethyl acetate. The organic phase is separated off, washed with water, dried with sodium sulphate and filtered. The filtrate is concentrated and the residue is purified by chromatography (silica gel column; eluent: ethyl acetate/cyclohexane 1:3).

1.8 g (21% of theory) of 2-(3-allylthio-4-chloro-phenyl)-3-ethylidene-4, 5,6,7-tetrahydro-2H-isoindol-1-one of refractive index $n_D^{20}$=1.5945 are obtained.

EXAMPLE 4

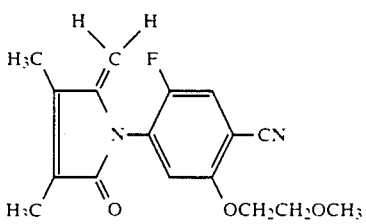

(Process (d))

0.17 g (6 mmol) of sodium hydride (80% strength) and 0.60 g (2.3 mmol) of 1-(2,5-difluoro-4-cyanophenyl)3, 4-dimethyl-5-methylene-pyrrol-(1H)2-one are added in succession to 1 ml of 2-methoxy-ethanol, while stirring, and the mixture is stirred at 20° C. for 12 hours. It is then slowly diluted to about 5 times the volume with water and the product obtained as crystals is isolated by filtration with suction.

0.50 g (68% of theory) of 1-(2-fluoro-4-cyano-5-(2-methoxy-ethoxy)-phenyl)-3, 4-dimethyl-5-methylene-pyrrol-(1H)2-one of melting point 78° C. is obtained.

The compounds of the formula (I) shown in the following Table 2 can also be prepared, for example, analogously to Examples 1 to 4 and in accordance with the general description of the preparation processes according to the invention.

TABLE 2

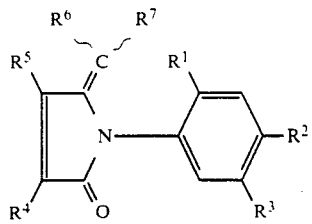

Preparation Examples for the compounds of the formula (I)

| Example No. | $R^1$ | $R^2$ | $R^3$ | $R^4$ | $R^5$ | $R^6$ | $R^7$ | Physical data |
|---|---|---|---|---|---|---|---|---|
| 5 | F | Cl | $O(CH_2CH_2O)_2C_2H_5$ | $CH_3$ | $CH_3$ | H | H | $^1$H-NMR (CDCl$_3$, δ, ppm): 1.96 (CH$_3$), 2.10 (CH$_3$) |
| 6 | F | Cl | $O(CH_2CH_2O)_2C_2H_5$ | $CH_3$ | $CH_3$ | $C_2H_5$ | H | $n_D^{20}$: 1.5484 |
| 7 | F | Cl | $O(CH_2CH_2O)_2C_2H_5$ | $-(CH_2)_4-$ | | $CH_3$ | H | $n_D^{20}$: 1.5530 |
| 8 | F | Cl | $O(CH_2CH_2O)_2C_2H_5$ | $CH_3$ | $CH_3$ | $CH_3$ | $CH_3$ | $n_D^{20}$: 1.5485 |
| 9 | F | Cl | $O(CH_2CH_2O)_2C_2H_5$ | $-(CH_2)_4-$ | | $C_2H_5$ | H | $n_D^{20}$: 1.5486 |
| 10 | F | Cl | $O(CH_2CH_2O)_2C_2H_5$ | $CH_3$ | $CH_3$ | $CH_3$ | H | $^1$H-NMR (CDCl$_3$, δ, ppm): 1.42 (CH$_3$), 1.44 (CH$_3$) |
| 11 | F | Cl | $O(CH_2CH_2O)_2C_2H_5$ | $-(CH_2)_4-$ | | $CH_3$ | $CH_3$ | $n_D^{20}$: 1.5619 |
| 12 | H | $CH_3$ | Cl | $CH_3$ | $CH_3$ | H | H | mp: 97° C. |
| 13 | H | Cl | $SCH_2C\equiv CH$ | $-(CH_2)_4-$ | | H | H | $n_D^{20}$: 1.6247 |
| 14 | H | Cl | $SCH_2CH=CH_2$ | $-(CH_2)_4-$ | | H | H | $n_D^{20}$: 1.6228 |
| 15 | H | Cl | $SCH_2C\equiv CH$ | $-(CH_2)_4-$ | | $CH_3$ | H | $n_D^{20}$: 1.6160 |
| 16 | F | CN | F | $-(CH_2)_4-$ | | H | H | mp.: 124° C. |
| 17 | F | CN | $OCH_2C\equiv CH$ | $-(CH_2)_4-$ | | H | H | mp.: 146° C. |
| 18 | H | Cl | SH | $-(CH_2)_4-$ | | $CH_3$ | H | mp.: 85° C. |
| 19 | H | Cl | SH | $-(CH_2)_4-$ | | H | H | mp.: 70° C. |
| 20 | F | CN | $OCH_2CH=CH_2$ | $-(CH_2)_4-$ | | H | H | mp.: 117° C. |
| 21 | H | Cl | Cl | $CH_3$ | $CH_3$ | H | H | mp.: 120° C. |
| 22 | F | Cl | $O(CH_2CH_2O)_2C_2H_5$ | $-(CH_2)_4-$ | | H | H | mp.: 77° C. |
| 23 | H | CN | $OCH_2C\equiv CH$ | $-(CH_2)_4-$ | | H | H | mp.: 165° C. |
| 24 | H | CN | $OCH_2CH=CH_2$ | $-(CH_2)_4-$ | | H | H | mp.: 105° C. |
| 25 | F | CN | $OCH_2CH=CH_2$ | $-(CH_2)_4-$ | | H | H | mp.: 117° C. |
| 26 | F | CN | $OCH_2CH_2OCH_3$ | $-(CH_2)_4-$ | | H | H | mp.: 88° C. |

USE EXAMPLES

Example A

Post-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 1,000 l of water/ha. After three weeks, the degree of damage to the plants is rated in % damage in comparison to the development of the untreated control. The figures denote:

0% = no action (like untreated control)
100% = total destruction

In this test, for example, the compounds according to Preparation Examples 5, 6, 7 and 8 exhibit a very potent action against weeds, such as, for example, Amaranthus, Galium, Protulaca and Veronica, coupled with a good tolerance in respect of useful plants, such as, for example, wheat and rape.

Example B

Pre-emergence test

Solvent: 5 parts by weight of acetone
Emulsifier: 1 part by weight of alkylaryl polyglycol ether To produce a suitable preparation of active compound, 1 part by weight of active compound is mixed with the stated amount of sovent, the stated amount of emulsifier is added and the concentrate is diluted with water to the desired concentration.

Seeds of the test plants are sown in normal soil, and 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

In this test, for example, the compounds according to Preparation Examples 5, 6, 7, 9, 11 and 22 exhibit a very potent action against weeds, such as, for example, Cynodon, Setaria, Abutiton, Amaranthus, Chenopodium and Galium, coupled with a good tolerance in respect of culture plants, such as, for example, wheat, corn and soy beans.

Example C

Defoliation and desiccation of the leaves of cotton

Solvent: 30 parts by weight of dimethylformamide
Emulsifier: 1 part by weight of polyoxyethylene sorbitan monolaurate To produce a suitable preparation of active compound, 1 part by weight of active compound is mixed with the stated amounts of solvent and emulsifier and the mixture is made up to the desired concentration with water.

Cotton plants are grown in a greenhouse until the 5th true leaf has unfolded completely. In this stage, the plants are sprayed with the preparations of active compound until dripping wet. After 1 week, the shedding of leaves and the desiccation of the leaves are rated, in comparison with the control plants.

In this test, for example, the active compounds according to Preparation Examples (7), (9), (11) and (22) exhibit very pronounced desiccation of the leaves and very pronounced shedding of leaves.

It will be understood that the specification and examples are illustrative but not limitative of the present invention and that other embodiments within the spirit and scope of the invention will suggest themselves to those skilled in the art.

We claim:

1. An N-aryl-nitrogen heterocyclic compound of the formula $$\text{(I)}$$

in which $R^1$ represents hydrogen or halogen, $R^2$ represents cyano, nitro, fluorine, chlorine, bromine, iodine, alkyl, halogenoalkyl, alkoxy, halogenoalkoxy, alkylthio or halogenoalkylthio, $R^3$ represents halogen, hydroxyl or mercapto, or represents an optionally substituted radical selected from the group consisting of alkoxy, alkenyloxy, alkinyloxy, cycloalkoxy, alkylthio, alkenylthio, alkinylthio and cycloalkylthio, $R^4$ represents hydrogen, halogen or alkyl, $R^5$ represents hydrogen, halogen or alkyl, or together with $R^4$ represents alkanediyl, $R^6$ represents hydrogen or alkyl and $R^7$ represents hydrogen or alkyl, or together with $R^6$ represents alkanediyl, with the proviso that $R^2$ can represent chlorine only if either (a) $R^1$ represents hydrogen or at least one of the radicals $R^4$, $R^5$, $R^6$ and $R^7$ represents alkyl and at the same time $R^3$ represents halogen or mercapto or represents an optionally substituted radical selected from the group consisting of alkylthio, alkenylthio, alkinylthio and cycloalkylthio, or (b) $R^3$ represents halogen or represents alkoxyalkoxyalkoxy.

2. An N-aryl-nitrogen heterocyclic compound according to claim 1, in which $R^1$ represents hydrogen or fluorine, $R^2$ represents cyano, nitro, fluorine, chlorine, bromine, methyl, ethyl, methoxy, ethoxy, methylthio, ethylthio, halogenoalkyl having 1 or 2 carbon atoms and 1 to 5 halogen atoms, halogenoalkoxy having 1 or 2 carbon atoms and 1 to 5 halogen atoms or halogenoalkylthio having 1 or 2 carbon atoms and 1 to 5 halogen atoms, $R^3$ represents fluorine, chlorine, bromine, hydroxyl or mercapto, or represents in each case optionally substituted straight-chain or branched alkoxy or alkylthio having in each case up to 8 carbon atoms, the optical substituents being selected from the group consisting of fluorine, chlorine, bromine, cyano, carboxyl, $C_1$-$C_4$-alkoxy, $C_1$-$C_4$-alkoxy-$C_1$-$C_4$-alkoxy, $C_1$-$C_4$-alkylthio, $C_1$-$C_4$-alkyl-carbonyl, $C_1$-$C_4$-alkoxy-carbonyl, $C_3$-$C_6$-cycloalkoxy-carbonyl, $C_3$-$C_6$-cycloalkyl-$C_1$-$C_2$-alkoxy-carbonyl, $C_5$-$C_6$-cycloalkenyloxy-carbonyl, $C_5$-$C_6$cycloalkenyl-$C_1$-$C_2$-alkoxy-carbonyl and tetrahydrofuryl methoxy-carbonyl; or furthermore $R^3$ represents in each case optionally substituted and in each case optionally branched alkenyloxy, alkinyloxy, cycloalkoxy, alkenylthio, alkinylthio or cycloalkylthio having in each case up to 8 carbon atoms, the optional substituents being selected from the group consisting of fluorine, chlorine, bromine, cyano, carboxyl and $C_1$-$C_4$-alkoxy-carbonyl;

$R^4$ represents hydrogen or chlorine, or represents straight-chain or branched alkyl having 1 to 4 carbon atoms, $R^5$ represents hydrogen, chlorine or straight-chain or branched alkyl having 1 to 4 carbon atoms, or $R^5$ together with $R^4$ represents straight-chain or branched alkanediyl having 3 to 6 carbon atoms, $R^6$ represents hydrogen or straight-chain or branched alkyl having 1 to 4 carbon atoms and $R^7$ represents hydrogen or straight-chain or branched alkyl having 1 to 4 carbon atoms, or $R^7$, together with $R^6$, represents straight-chain or branched alkanediyl having 2 to 7 carbon atoms, with the proviso that $R^2$ can represent chlorine only if either (a) $R^1$ represents hydrogen or at least one of the radicals $R^4$, $R^5$, $R^6$ and $R^7$ represents alkyl and at the same time $R^3$ represents halogen or mercapto or represents an optionally substituted radical selected from the group consisting of alkylthio, alkenylthio, alkinylthio and cycloalkythio, or (b) $R^3$ represents halogen or represents alkoxyalkoxyalkoxy.

3. An N-aryl-nitrogen heterocyclic compound according to claim 1, in which $R^1$ represents hydrogen or fluorine, $R^2$ represents cyano, nitro, fluorine, chlorine, bromine, methyl, trifluoromethyl, methoxy, trifluoromethoxy, difluoromethoxy, chlorodifluoromethoxy, methylthio, trifluoromethylthio, difluoromethylthio or chlorodifluoromethylthio, $R^3$ represents fluorine, chlorine, bromine, hydroxyl or mercapto, or represents in each case optionally substituted methoxy, ethoxy, propoxy, isopropoxy, butoxy, isobutoxy, sec-butoxy, tert-butoxy, pentoxy, isopentoxy, sec-pentoxy, tert-pentoxy, hexyloxy, isohexyloxy, methylthio, ethylthio, propylthio, isopropylthio, butylthio, isobutylthio, sec-butylthio, tert-butylthio, pentylthio, isopentylthio, sec-pentylthio, tert-pentylthio, hexylthio or isohexylthio, the optional substituents being fluorine, chlorine, cyano, carboxyl, methoxy, ethoxy, propoxy, isopropoxy, methoxyethoxy, ethoxyethoxy, methylthio, ethylthio, propylthio, isopropylthio, methylcarbonyl, ethylcarbonyl, propylcarbonyl, isopropylcarbonyl, butylcarbonyl, isobutylcarbonyl, sec-butylcarbonyl, tert-butylcarbonyl, methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, cyclopropyloxycarbonyl, cyclopentyloxycarbonyl, cyclohexyloxycarbonyl, cyclopentenyloxycarbonyl, cyclohexenyloxycarbonyl, cyclopropylmethoxycarbonyl, cyclopentylmethoxycarbonyl, cyclohexylmethoxycarbonyl, cyclopentenylmethoxycarbonyl, cyclohexenylmethoxycarbonyl and tetrahydrofurylmethoxycarbonyl; or in which, furthermore, $R^3$ represents allyloxy or 1-methyl-, 2-methyl- or 3methylallyloxy, or represents propargyloxy or 1-methyl-, 3-methyl- or 1,1-dimethyl-propargyloxy, or represents cyclopropyloxy, cyclopentyloxy or cyclohexyloxy, or represents allylthio or 1-methyl-, 2-methyl- or 3-methyl-allylthio, or represents propargylthio or 1-methyl-, 3-methyl- or 1,1-dimethylpropargylthio, or represents cyclopropylthio, cyclopentylthio or cyclohexylthio, which are in each case optionally substituted by fluorine and/or chlorine;

$R^4$ represents hydrogen, methyl, ethyl, propyl or isopropyl, $R^5$ represents hydrogen, methyl, ethyl, propyl or isopropyl, or together with $R^4$ represents propane1,3-diyl, butane-1,3-diyl, butane-1,4-diyl or 2,2-dimethyl-propane-1,3-diyl, $R^6$ represents hydrogen, methyl, ethyl, propyl, isopropyl, butyl, isobutyl, sec-butyl or tert-butyl and $R^7$ represents hydrogen, methyl, ethyl or propyl, or together with $R^6$ represents ethane-1,2-diyl, propane-1,3-diyl, butane-1,3-diyl, butane-1,4-diyl, pentane1,4-diyl or pentane-1,5-diyl, with the proviso that $R^2$ can represent chlorine only if either (a) $R^1$ represents hydrogen or at least one of the radicals $R^4$, $R^5$, $R^6$ and $R^7$ represents alkyl and at the same time $R^3$ represents halogen or mercapto or represents a radical, in each case optionally substituted, from the series comprising alkylthio, alkenylthio, alkinylthio and cycloalkylthio, or (b) $R^3$ represents halogen or represents alkoxyalkoxyalkoxy.

4. An N-aryl-nitrogen heterocyclic compound according to claim 3, in which
$R^1$ represents hydrogen or fluorine,
$R^2$ represents chlorine, cyano or methyl,
$R^4$ represents methyl,
$R^5$ represents methyl or, together with $R^4$, represents $-(CH_2)_4-$, and
$R^6$ and $R^7$ independently of one another represent hydrogen, methyl or ethyl,
with the proviso that $R^2$ can represent chlorine only if either (a) $R^1$ represents hydrogen or at least one of the radicals $R^4$, $R^5$, $R^6$ and $R^7$ represents alkyl and at the same time $R^3$ represents halogen or mercapto or represents a radical, in each case optionally substituted, from the series comprising alkylthio, alkenylthio, alkinylthio and cycloalkylthio, or (b) $R^3$ represents halogen or represents alkoxyalkoxyalkoxy.

5. A herbicidal and plant growth-regulating composition comprising an amount effective therefor of a compound according to claim 1 and a diluent.

6. A compound according to claim 1, wherein such compound is 1-(2-fluoro-4-chloro-5-ethoxyethoxyethoxy-phenyl)-3, 4-dimethyl-5-methylene-pyrrol-(1H)2-one of the formula

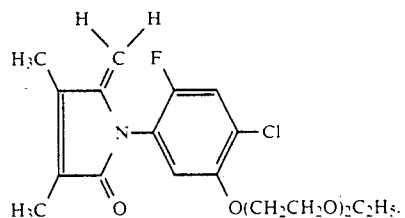

7. A compound according to claim 1, wherein such compound is 1-(2-fluoro-4-chloro-5-ethoxyethoxy-phenyl)-3, 4-dimethyl-5-propylidene-pyrrole-(1H)2-one of the formula

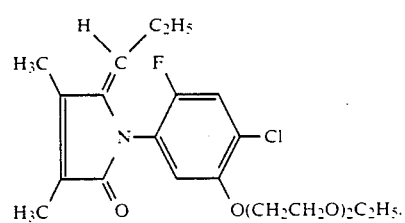

8. A compound according to claim 1, wherein such compound is 2-(2-fluoro-4-chloro-5-ethoxyethoxy-phenyl)-3-ethylidene-4, 5,6,7,-tetrahydro-2H-isoindol-1-one of the formula

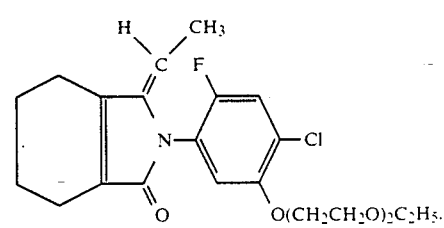

9. A compound according to claim 1, wherein such compound is 1-(2-fluoro-4-chloro-5-ethoxyethoxy-phenyl)-3, 4-dimethyl-5-isopropylidene-pyrrol-(1H)2-one of the formula

10. A compound according to claim 1, wherein such compound is 2-(2-fluoro-4-chloro-5-ethoxyethoxyethoxy-phenyl)-3-propylidene-4, 5,6,7-tetrahydro-2H-isoindol-1-one of the formula

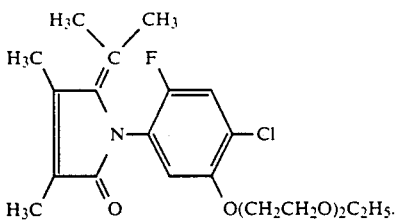

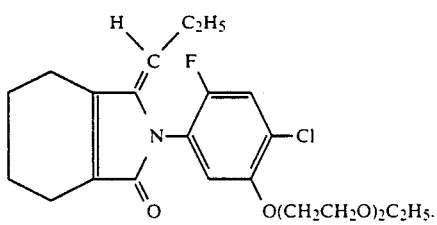

11. A compound according to claim 1, wherein such compound is 2-(2-fluoro-4-chloro-5-ethoxyethoxyethoxy-phenyl)-3-isopropylidene-4, 5,6,7-tetrahydro-2H-isoindol-1-one of the formula

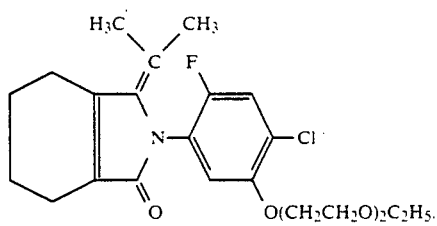

12. A compound according to claim 1, wherein such compound is 2-(2-fluoro-4-chloro-5-ethoxyethoxyethoxy-phenyl-3-methylene-4, 5,6,7-tetrahydro-2H-isoindol-1-one of the formula

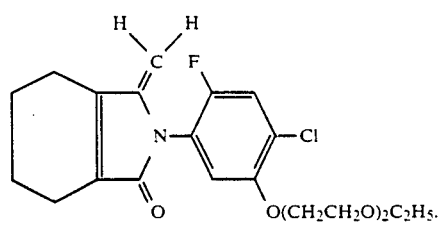

13. A method of excluding unwanted vegetation which comprises applying to such vegetation or to a locus from which it is desired to exclude such vegetation a herbicidally effective amount of a compound according to claim 1.

14. The method according to claim 13, wherein such compound is 1-(2-fluoro-4-chloro-5-ethoxyethoxyethoxy-phenyl)-3, 4-dimethyl-5-methylene-pyrrol(1H)2-one, 1-(2-fluoro-4-chloro-5-ethoxyethoxyethoxy-phenyl)-3, 4-dimethyl-5-propylidene-pyrrole-(1H)2-one, 2-(2-fluoro-4-chloro-5-ethoxyethoxyethoxy-phenyl)-3-ethylidene-4, 5,6,7,-tetrahydro2H-isoindol-1-one, 1-(2-fluoro-4-chloro-5-ethoxyethoxyethoxy-phenyl)-3, 4-dimethyl-5-isopropylidene-pyrrol-(1H)2-one, 2-(2-fluoro-4-chloro-5-ethoxyethoxyethoxy-phenyl)-3-propylidene-4, 5,6,7-tetrahydro2H-isoindol-1-one, 2-(2-fluoro-4-chloro-5-ethoxyethoxyethoxy-phenyl)-3-isopropylidene-4, 5,6,7-tetrahydro2H-isoindol-1-one, or 2-(2-fluoro-4-chloro-5-ethoxyethoxyethoxy-phenyl-3-methylene-4, 5,6,7-tetrahydro-2H-isoindol-1-one.

15. A method of regulating the growth of a plant which comprises applying to such plant or to a locus in which said plant is growing or is to be grown a plant growth-regulating effective amount of a compound according to claim 1.

16. The method according to claim 15, wherein such compound is 1-(2-fluoro-4-chloro-5-ethoxyethoxyethoxy-phenyl)-3, 4-dimethyl-5-methylene-pyrrol(1H)2-one, 1-(2-fluoro-4-chloro-5-ethoxyethoxyethoxy-phenyl)-3, 4-dimethyl-5-propylidene-pyrrole-(1H)2-one, 2-(2-fluoro-4-chloro-5-ethoxyethoxyethoxy-phenyl)-3-ethylidene-4, 5,6,7,-tetrahydro2H-isoindol-1-one, 1-(2-fluoro-4-chloro-5-ethoxyethoxyethoxy-phenyl)-3, 4-dimethyl-5-isopropylidenepyrrol-(1H)2-one, 2-(2-fluoro-4-chloro-5-ethoxyethoxyethoxy-phenyl)-3-propylidene-4, 5,6,7-tetrahydro2H-isoindol-1-one, 2-(2-fluoro-4-chloro-5-ethoxyethoxyethoxyphenyl)-3-isopropylidene-4, 5,6,7-tetrahydro2H-isoindol-1-one, or 2-(2-fluoro-4-chloro-5-ethoxyethoxyethoxy-phenyl-3-methylene-4, 5,6,7-tetrahydro-2H-isoindol-1-one.

17. An N-aryl-nitrogen heterocyclic compound of the formula

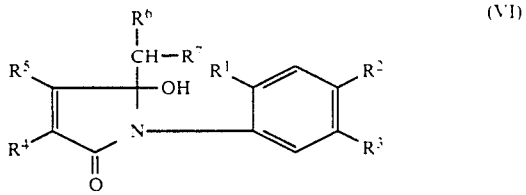

in which $R^1$ represents hydrogen or halogen, $R^2$ represents cyano, nitro, fluorine, chlorine, bromine, iodine, alkyl, halogenoalkyl, alkoxy, halogenoalkoxy, alkylthio or halogenoalkylthio, $R^3$ represents halogen, hydroxyl or mercapto, or represents an optionally substituted radical selected from the group consisting of alkoxy, alkenyloxy, alkinyloxy, cycloalkoxy, alkylthio, alkenylthio, alkinylthio and cycloalkylthio, $R^4$ represents hydrogen, halogen or alkyl, $R^5$ represents hydrogen, halogen or alkyl, or together with $R^4$ represents alkanediyl, $R^6$ represents hydrogen or alkyl and $R^7$ represents hydrogen or alkyl, or together with $R^6$ represents alkanediyl, with the proviso that $R^2$ only represents chlorine if either (a) $R^1$ represents hydrogen or at least one of the radicals $R^4$, $R^5$, $R^6$ and $R^7$ represents alkyl and at the same time $R^3$ represents halogen or mercapto or represents an optionally substituted radical selected from the group consisting of alkylthio, alkenylthio, alkinylthio and cycloalkylthio, or (b) $R^3$ represents halogen or represents alkoxyalkoxyalkoxy.

* * * * *

UNITED STATES PATENT AND TRADEMARK OFFICE
CERTIFICATE OF CORRECTION

PATENT NO. : 5,045,108

DATED : September 3, 1991

INVENTOR(S) : Elbe et al.

It is certified that error appears in the above-identified patent and that said Letters Patent is hereby corrected as shown below:

Title Page item [57] ABSTRACT: Line 8 delete " halogeneoalkylthio " and substitute -- halogenoalkylthio --

Col. 60, line 52 Delete " cycloalkythio " and substitute - cycloalkylthio --

Signed and Sealed this

Twenty-eighth Day of September, 1993

Attest:

BRUCE LEHMAN

Attesting Officer Commissioner of Patents and Trademarks